US008754200B2

(12) United States Patent
Perez et al.

(10) Patent No.: US 8,754,200 B2
(45) Date of Patent: Jun. 17, 2014

(54) MEG1 ENDOSPERM-SPECIFIC PROMOTERS AND GENES

(75) Inventors: Pascual Perez, Chanonat (FR); José Gutierrez-Marcos, Oxford (GB); Hugh Dickinson, Oxford (GB)

(73) Assignee: Biogemma, Paris (FR)

( * ) Notice: Subject to any disclaimer, the term of this patent is extended or adjusted under 35 U.S.C. 154(b) by 1044 days.

(21) Appl. No.: 12/795,898

(22) Filed: Jun. 8, 2010

(65) Prior Publication Data

US 2010/0306876 A1 Dec. 2, 2010

Related U.S. Application Data

(62) Division of application No. 10/578,126, filed as application No. PCT/EP2004/052760 on Nov. 2, 2004, now Pat. No. 7,745,697.

(30) Foreign Application Priority Data

Nov. 3, 2003 (EP) .................................... 03292739

(51) Int. Cl.
 *C12N 15/82* (2006.01)
(52) U.S. Cl.
 USPC .......... 536/24.1; 800/279; 800/287; 800/306; 800/320; 800/322; 435/320.1; 435/419
(58) Field of Classification Search
 None
 See application file for complete search history.

(56) References Cited

FOREIGN PATENT DOCUMENTS

| WO | WO-99/50427 A2 | 10/1999 |
| WO | WO-02/36788 A2 | 5/2002 |
| WO | WO-03/078580 | 9/2003 |

OTHER PUBLICATIONS

An, et al., "Development of plant promoter expression vectors and their sse for analysis of differential activity of nopaline synthase promoter in transformed tobacco cells", Plant Physiology, vol. 81, 1986, pp. 86-91.
Anderson, et. al., "The characterization and comparative analysis of high-molecular-weight glutenin genes from genomes A and B of a hexaploid breat wheat", Theor Appl Genet, vol. 77, 1989, pp. 689-700.
Allison, et al., "The nucleotide sequence of the coding region of tobacco etch virus genomic RNA: evidence for the synthesis of a single polyprotein", Virology, No. 154, 1986, pp. 9-20.
Berg, et al., "The galvanization of biology: a growing appreciation for the roles of zinc", Science, vol. 271, 1996, pp. 1081-1085.
Bevan, et al., "A chimaeric antibiotic resistance gene as a selectable marker for plant cell transformation", Nature, vol. 304, 1983, pp. 184-187.
Bolchi, et al., "Coordinate modulation of maize sulfate permease and ATP sulfurylase mRNAs in response to variations in sulfur nutritional status: steereospecific down-regulation by L-cysteine", Plant Molecular Biology, vol. 39, 1999, pp. 527-537.
Bonello, et al., "Esr genes show different levels of expression in the same region of maize endosperm", Gene, vol. 246, 2000, pp. 219-227.
Callis, et al., "Introns increase gene expression in cultured maize cells", Genes Dev., vol. 1:1183, 1987, pp. 1183-1200.
Cassab, G. I., "Plant cell wall proteins", Annual Review of Plant Physiology and Plant Molecular Biology, vol. 49, 1998, pp. 281-309.
Cheng, et al., "The miniature1 seed locus of maize encodes a cell wall invertase required for normal development of endosperm and maternal cells in the pedicel", Plant Cell, vol. 8, 1996, pp. 971-983.
Christensen, et al., "Ubiquitin promoter-based vectors for high-level expression of selectable and/or screenable marker genes in monocotyledonous plants", Transgenic Research, vol. 5, 1996, pp. 213-218.
Chupeau, et al., "Transgenic plants of lettuce (*Lactuca sativa*) obtained through electroporation of protoplasts", Biotechnology, vol. 7, 1989, pp. 503-508.
Cordts, et al., "ZmES gene encode peptides with structural homology to defensins and are specifically expressed in the female gametophyte", Plant Journal, vol. 25, 2001, pp. 103-114.
Costa, et al., "The globby1 (glo-1-1) mutation disrupts nuclear and cell division in the developing maize seed causing aberrations in endosperm cell fate and tissue differentiation", Development, vol. 130, No. 20, 2003, pp. 5009-5017.
Deyeyser, et al., "Evaluation of selectable markers for rice transformation", Plant Physiology, vol. 90, 1988, pp. 217-223.
Della-Cioppa, et al., "Protein trafficking in plant cells", Plant Physiology, vol. 84, 1987, pp. 965-968.
de Oliveira, et al., "Differential expression of five arabidopsis genes encoding glycine-rich proteins", Plant Cell, vol. 2, 1990, pp. 427-436.
Depicker, et al., "Effect of T-DNA configuration on transgene expression", Mol. Gen. Genet., vol. 235, 1992, pp. 389-396.
Depigny-This, et. al., "The cruciferin gene family in radish", Plant Molecular Biology, vol. 20, 1992, pp. 467-479.
Domingo, et al., "Identification of a novel peptide motif that mediates cross-linking of proteins to cell walls", Plant Journal, vol. 20, No. 5, 1999, pp. 563-570.
Eichholtz, et al., "Expression of mouse dihydrofolate reductase gene confers methotrexate resistance in transgenic petunia plants", Somatic Cell and Molecular Genetics, vol. 13, 1987, pp. 67-76.
Elroy-Stein, et al., "Cap-independent translation of mRNA conferred by encephalomyocarditis virus 5' sequence improves the performance of the vaccinia virus/bacteriophase T7 hybrid expression system", Proc. Natl. Acad. Sci., vol. 86, 1989, pp. 6126-6130.
Finer, et al., "Development of the particle inflow gun for DNA delivery to plant cells", Plant Cell Reports, vol. 11, 1992, pp. 323-328.
Franck, et al., "Nucelotide sequence of cauliflower mosaic virus DNA", Cell, vol. 21, 1980, pp. 285-294.
Gallie, et. al., "Eukaryotic viral 5'-leader sequences act as translational enhancers in eukaryotes and prokaryotes", Molecular Biology of RNA, 1989, pp. 237-256.

(Continued)

*Primary Examiner* — Russell Kallis
(74) *Attorney, Agent, or Firm* — Novak Druce Connolly Bove + Quigg LLP

(57) ABSTRACT

The present invention relates to promoters that enable gene expression which is both specific to the endosperm and early during the development of the endosperm, as well as nucleic acid molecules encoding basal endosperm transfer cell layer (BETL) proteins.

12 Claims, 13 Drawing Sheets

(56) References Cited

OTHER PUBLICATIONS

Gleave, A.P., "A versatile binary vector system with a T-DNA organisational structure conducive to efficient integration of cloned DNA into the plant genome", Plant Molecular Biology, vol. 20, 1992, pp. 1203-1207.
Gomez, et al., "Establishment of cereal endosperm expression domains: identification and properties of a maize transfer cell-specific transcription factor, ZmMRP-1", Plant Cell, vol. 14, 2002, pp. 599-610.
Gritz, et al., "Plasmid-encoded hygromycin B resistance: the sequence of hygromycin B phosphotransferase gene and its expression in *Escherichia coli* and *Saccharomyces cerevisiae*", Gene, vol. 25, 1983, pp. 179-188.
Guerche, et al., "Genetic transformation of oilseed rape (*Brassica napus*) by the Ri T-DNA of *Agrobacterium rhizogenes* and analysis of inheritance of the transformed phenotype", Mol. Gen. Genet., vol. 206, 1987, pp. 382-386.
Gutierrez-Marcos, et al., "Imprinting in the endosperm: a possible role in preventing wide hybridization", Phil. Trans. R. Soc. Lond B, vol. 358, 2003, pp. 1105-1111.
Hagiwara, et al., "Screening for imprinted genes by allelic message display: Identification of a paternally expressed gene *Impact* on mouse chromosome 18", Prod. Natl. Acad. Sci. USA, vol. 94, 1997, pp. 9249-9254.
Hauptmann, et al., "Evaluation of selectable markers for obtaining stable transformants in the gramineae", Plant Physiology, vol. 86, 1988, pp. 602-606.
Hueros, et al, "Molecular characterization of BET1, a gene expressed in the endosperm transfer cells of maize", Plant Cell, vol. 7, 1995, pp. 747-757.
Hueros, et al., "Evidence for factors regulating transfer cell-specific expression in maize endosperm", Plant Mol Biol., vol. 41, 1999, pp. 403-414.
Hueros, et al., "Identification of a promoter sequence from the BETL1 gene cluster able to confer transfer-cell-specific expression in transgenic maize", Plant Physiology, vol. 121, 1999, pp. 1143-1152.
Ishida, et al., "Identification of a promoter sequence from the BETL1 gene cluster able to confer transfer-cell-specific expression in transgenic maize", Nature Biotechnology, vol. 14, 1996, pp. 745-750.
Jang, et al., "Hexokinase as a sugar sensor in higher plants", Plant Cell, vol. 9, 1997, pp. 5-19.
Jefferson, et al., "GUS fusions: *B*-glucuronidase as a sensitive and versatile gene fusion marker in higher plants", EMBO Journal, vol. 6, 1987, pp. 3901-3907.
Jefferson, R.A., "The GUS reporter gene system", Nature, vol. 342, 1989, pp. 837-838.
Jenkins, et al., "Dehiscence-related expression of an *Arabidopsis thaliana* gene encoding a polygalactoronase in transgenic plant sof *Brassica napus*", Plant Cell and Environment, vol. 22, 1999, pp. 159-167.
Jobling, et al., "Enhanced translation of chimaeric messenger RNAs containing a plant viral untranslated leader sequence", Nature, vol. 325, 1987, pp. 622-625.
Jones, et al., "Effective vectors for transformation, expression of heterologous genes, and assaying transposon excision in transgenic plants", Transgenic Research, vol. 1, 1992, pp. 285-297.
Jouanin, et al., "Transfer of a 4.3-kb fragment of the tl-DNA of *Agrobacterium rhizogenes* strain A4 confers the pRi transformed phenotype to regenerated tobacco plants", Plant Science, vol. 53, 1987, pp. 53-63.
Kay, et al., "Duplication of CaMV 35S promoter sequences creates a strong enhanced for plant genes", Science, vol. 236, 1987, pp. 1299-1302.
Laemmli, U.K., "Cleavage of structural proteins during the assembly of the head of bacteriophase T4", Nature, vol. 227, 1970, pp. 680-685.
Lobreaux, et al., "Iron induces ferritin synthesis in maize plantlets", Plant Molecular Biology, vol. 19, 1992, pp. 563-575.
Lommel, et al., "Identification of the maize mottle virus capsid protein cistron and characterization of its subgenomic messenger RNA", Virology, vol. 81, 1991, pp. 382-385.
Maas, et al., "The combination of a novel stimulatory element in the first exon of the maize *Shrunken-1* gene with the following intron 1 enhances reporter gene expression up to 1000-fold", Plant Molecular Biology, vol. 16, 1991, pp. 199-207.
Macejak, et al., "Internal initiation of translation mediated by the 5' leader of a cellular mRNA", Nature, vol. 353, 1991, pp. 90-94.
Knight, et al., "Molecular cloning of starch synthase I from maize (W64) endosperm and expression in *Escherichia coli*", The Plant Journal, vol. 14, No. 5, 1998, pp. 613-622.
McElroy, et al., "Isolation of an efficient actin promoter for use in rice transformation", Plant Cell, vol. 2, 1990, pp. 163-171.
Meijer, et al., "Transgenic rice cell lines and plants: expression of transferred chimeric genes", Plant Molecular Biology, No. 16, 1991, pp. 807-820.
Gao, , et al., "Independent genetic control of maize starch-branchingt enzymes IIa and IIb", Plant Physiology, vol. 114, 1997, pp. 69-78.
Morris, et al., "The nucleotide sequence of the infectious cloned DNA component of tobacco yellow dwarf virus reveals features of geminiviruses infecting monocotyledonous plants", Virology, vol. 187, 1992, pp. 633-642.
Mullis, et al., "Specific synthesis of DNA in Vitro via a polymerase-catalyzed chain reaction", Methods of Enzymology, vol. 155, 1987, pp. 335-350.
Murashige, et al., "A revised medium for rapid growth and bio assays with tobacco tissue cultures", Physiology Plant, vol. 15, 1962, pp. 473-497.
Neff, et al., "dCAPS, a simple technique for the genetic analysis of single nucleotide polymorphisms: experimental applications in *Arabidopsis thaliana* genetics", The Plant Journal, vol. 14, No. 3, 1998, pp. 387-392.
Ohta, et al., "Construction and expression in tobacco of a β-Glucuronidase (GUS) reporter gene containing an intron within the coding sequence", Plant Cell Physiology, No. 31, 1990, pp. 805-813.
O'Sullivan, et al., "A maize bacterial artificial chromosome (BAC) library from the European flint inbred line F2", Theor. Appl. Genet., vol. 103, 2001, pp. 425-432.
Pang, et al., "An improved green fluorescent protein gene as a vital marker in plants", Plant Physiology, vol. 112, 1996, pp. 893-900.
Poole, et al., "The engrailed locus of *Drosophila*: structural analysis of an embryonic transcript", Cell, vol. 40, 1985, pp. 37-43.
Robert, et al., "Tissue-specific expression of a wheat high molecular weight glutenin gene in transgenic tobacco", Plant Cell, vol. 1, 1989, pp. 569-578.
Serna, et al., "Maize endosperm secretes a novel antifungal protein into adjacent maternal tissue", Plant Journal, vol. 25, No. 6, 2001, pp. 687-698.
Sevilla, et al., "Analysis of ZmAE3 upstream sequences in maize endosperm and androgenic embryos", Plant Molecular Biology, vol. 16, 2003, pp. 1-8.
Snowden, et al., "Intron position affects expression from the *tpi* promoter in rice", Plant Molecular Biology, vol. 31, 1996, pp. 689-692.
Taliercio, et al., "Isolation, characterization and expression analyses of two cell wall invertase genes in maize", Journal of Plant Physiol., vol. 155, 1999, pp. 197-204.
Greene, et al., "Maize endosperm ADP-glucose pyrophosphorylase SHRUNKEN2 and BRITTLE2 subunit interactions", The Plant Cell, vol. 10, 1998, pp. 1295-1306.
Vancanneyt, et al., "Construction of an intron-containing marker gene: splicing of the intron in transgenic plants and its use in monitoring early events in *Agrobacterium*-mediated plant transformation", Mol. Gen. Genet. vol. 220, 1990, pp. 245-250.
von Heijne, G., "A new method for predicting signal sequence cleavage sites", Nucelic Acids Research, vol. 14, 1986, pp. 4683-4690.
White, et al., "A cassette containing the bar gene of *Streptomyces hygroscopicus*: a selectable marker for plant transformation". Nucleic Acids Research, vol. 18, No. 4, 1990, p. 1062.
Yoder, et al., "Transformation systems for generating marker-free transgenic plants", Biotechnology, vol. 12, 1994, pp. 263-267.

(56) References Cited

OTHER PUBLICATIONS

Zhang, et al., "The effect of auxin on cytokinin levels and metabolism in transgenic tobacco tissue expressing an *ipt* gene", Planta, vol. 196, 1995, pp. 84-94.

Whitelaw, C. A., et al., "PUII077TD ZM_0.6_1.0 KB *Zea mays* genomic clone ZMMBTa0591N09, genomic serve sequence", Aug. 25, 2003, Accession No. CG044206.

Whitelaw, C.A., et al., "PUFGU88TB ZM_0.6_1.0_KB *Zea mays* genomic clone ZMMBTa3166007, DNA sequence", Mar. 19, 2003, Accession No. BZ785501.

Genoplante, QBI17g05.xg QBI *Zea mays* cDNA clone QBI17g05, mRNA sequence, Jul. 18, 2003, Accession No. CF006083.

Genoplante, "QBI19h06.xg QBI *Zea mays* cDNA clone QBI19h06, mRNA sequence", Jul. 18, 2003, Accession No. CF006331.

Genoplante, "QBI23b02.xg QBI *Zea mays* cDNA clone QBI23b02, mRNA sequence", Jul. 18, 2003, Accession No. CF006827.

Walbot, V., "687010E11.x1 687—Early embryo from Delaware *Zea mays* cDNA, mRNA sequence", Apr. 3, 2000, Accession No. AW062022.

Singh, J.A., et al., Zm04_09f06_R Zm04_AAFC_ECORC_cold_stressed_maize_seedlings *Zea may* cDNA clone Zm04_09f06, mRNA sequence, Feb. 28, 2001, Accession No. BG320929.

Whitelaw, C.A., et al., "PUBAP16TD ZM_0.6_1.0_KB *Zea mays* genomic clone ZMMBTa011D08, DNA sequence", Feb. 6, 2003, Accession No. BZ671532.

Gutierrez-Marcos, et al., "Maternally expressed gene 1 is a novel maize endosperm transfer cell-specific gene with a maternal parent-of-origin pattern of expression", The Plant Cell, vol. 16, 2004, pp. 1288-1301.

Sambrook et al., Molecular Cloning, A Laboratory Manual, Cold Spring Harbour Laboratory Press, pp. 9.54-9.62 (1989).

Breyne, Peter et al., "Effect of T-DNA configuration on transgene expression" Mol. Gen. Genet, vol. 235, pp. 389-396, 1992.

MEG1 ENDOSPERM-SPECIFIC PROMOTERS AND GENES

RELATED APPLICATIONS

This application is a divisional application of application Ser. No. 10/578,126 filed on Jul. 17, 2006, now U.S. Pat. No. 7,745,697, which is the national stage of Application No. PCT/EP2004/052760 filed Nov. 2, 2004, which claims priority of Application No. 03292739.4 filed on Nov. 3, 2003 in the European Patent Office.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 11887_21_Rev_Sequence_List. The size of the text file is 35 kb, and the text file was created on Nov. 13, 2012.

The present invention relates to controlling the expression of genes during the development of the endosperm. It concerns in particular nucleic acid molecules which enable expression which is both specific to the endosperm and early during the development of the endosperm, as well as nucleic acid molecules encoding basal endosperm transfer cell layer (BETL) proteins.

The endosperm, a characteristic formation of Angiosperm seeds, is a nutritive tissue for the embryo. The maize endosperm originates with series of free-nuclear divisions, followed by cellularisation and the subsequent formation of a range of functional cellular domains. This tissue is complex in its structure and development, in particular in cereals.

The endosperm is the main storage organ in maize seeds, nourishing the embryo while the seed develops, and providing nutrients to the seedling on germination. Thus, the uptake of assimilates by the growing endosperm is a critical process in seed development.

The central area of the endosperm consists of large cells with vacuoles, which store the reserves of starch and proteins, whilst the region surrounding the embryo is distinguished by rather small cells, occupied for the major part by cytoplasm.

The Basal Endosperm Transfer Layer (BETL) area is highly specialized to facilitate uptake of solutes during grain development. These transfer cells of the basal endosperm have specialised internal structures adapted to absorb solutes from the maternal pedicel tissue, and translocate these products to the developing endosperm and embryo. Usually, BETL genes are expressed between 8 to 20 days after pollination (DAP).

The international patent application WO 99/50427 reports Basal Endosperm Transfer cell Layer genes and regulatory sequences thereof.

However, there is still a need for regulatory sequences specific to the endosperm.

The authors of the present invention have now isolated novel promoter nucleotide sequences that enable expression of the coding sequences to which they can be linked, which is specific to the endosperm in Angiosperm seeds and which intervenes particularly in the early stage of the development of the endosperm. These novel promoter nucleotide sequences are useful as an alternative to the few promoters described in the literature.

Such promoter sequences are particularly useful for targeting or regulating the expression of genes of interest.

Interestingly, the nucleotide sequences having promoter activity according to the invention have a maternal parent-of-origin pattern of expression so the genes under transcriptional control of these promoters are preferentially expressed through the maternal allele during early endosperm development.

Advantageously, these nucleotide sequences having promoter activity are active as early as 4 DAP, when maternally inherited.

Surprisingly, the authors found that the proteins encoded by the genes related to these promoter sequences are implicated in the mechanism of pathogen resistance and/or endosperm development.

The present invention relates to an isolated nucleic acid molecule having promoter activity specific to the endosperm that comprises a DNA sequence selected from the group consisting of:

(a) a sequence as depicted in any one of SEQ ID No: 1 to 3 (promoter MEG1-1 (pMEG1-1), promoter MEG1-2 (pMEG1-2), and promoter MEG1-3 (pMEG1-3), respectively);

(b) a fragment of a sequence as defined in (a), wherein said sequence has promoter activity specific to the endosperm;

(c) a sequence that has at least 70% sequence identity with a sequence as defined in (a), wherein said sequence has promoter activity specific to the endosperm;

(d) a sequence hybridizing with the complementary strand of a sequence as defined in (a) and/or (b) under stringent conditions, wherein said sequence has promoter activity specific to the endosperm; and (e) a sequence that comprises a nucleotide sequence which is conserved among at least two of SEQ ID No: 1 to 3.

As used herein, the term "conserved" sequence refers to a nucleotide stretch that shows 100% identity between at least two sequences of reference. Preferably said conserved sequence is found in all of the three sequences SEQ ID No: 1 to 3. A sequence alignment of SEQ ID No: 1 to 3 is shown in FIG. 14.

According to an embodiment, said conserved sequence comprises 10 contiguous nucleotides from SEQ ID No: 1, SEQ ID No: 2 or SEQ ID No: 3, preferably 15, 20, 25, or 30 contiguous nucleotides. Preferably, the sequence as defined in alternative (e) comprises 5' ATATAGATAGATATAG-CAAATTCACCAAATAATATAG 3' (SEQ ID No: 57). More preferably said sequence consists in SEQ ID No: 57. However, any conserved sequence, or a combination of conserved sequences, as shown in FIG. 14 is within the scope of the invention.

According to another embodiment, said sequence as defined in alternative (e) comprises a motif of 9 contiguous nucleotides from SEQ ID No: 1, SEQ ID No: 2 or SEQ ID No: 3, wherein nucleotides 1-3 and 7-9 of said motif are conserved among at least two, preferably three, of SEQ ID No: 1 to 3, and nucleotides 4-6 may be variable.

Particularly, the nucleic acid molecule according to the invention enables expression (promoter activity) which is both specific to the endosperm, more particularly to the BETL, and early during the development of the endosperm.

"Promoter activity specific to the endosperm" means, as used in the present invention, that the promoter is predominantly expressed in the endosperm, and preferably exclusively expressed in the endosperm.

"Early during the development of the endosperm" means that expression of the promoter occurs from the very first days after pollination, preferably as early as the fourth day after pollination.

The various nucleotide sequences of the invention can be of artificial origin or not. They may be DNA sequences obtained by screening banks of sequences by means of probes produced on the basis of SEQ ID No: 1, 2, 3, 5, 7, 9, 11, 13, and 15. Such banks can be prepared by conventional techniques of molecular biology, known to persons skilled in the art.

The nucleotide sequences according to the invention can also be prepared by chemical synthesis, or by mixed methods including the chemical or enzymatic modification of sequences obtained by screening banks. According to an embodiment of the invention, a nucleic acid molecule having such a promoter activity consists in SEQ ID No: 1 (pMEG1-1), SEQ ID No: 2 (pMEG1-2), or SEQ ID No: 3 (pMeg1-3).

By reference to these promoter sequences, a "fragment" denotes a sequence, particularly a DNA sequence, which has a reduced length with regard to said sequence of reference.

Such a fragment, according to the invention, has promoter activity specific to the endosperm, preferentially specific to the BETL, and contains at least 15, 25, 35, 37, 50, 75, 91, 95, 100, 121, 122, 127, 150, 200, 220, 240, 250, 270, 300, 350, 360 or 365 consecutives nucleotides of the DNA sequence of reference.

A preferred fragment contains the region defined by nucleotides 1 to 121 of SEQ ID No: 1, which corresponds to the sequence shown in SEQ ID No: 4, or contains the region defined by nucleotides 1 to 127 of SEQ ID No: 1, which corresponds to the sequence shown in SEQ ID No: 59.

Are also preferred fragments the regions defined by nucleotides 26 to 120 of SEQ ID No:4 and 29 to 119 of SEQ ID No:4.

A fragment according to the invention may also be obtained by fusion of at least two consecutive regions of a DNA sequence of reference. An example of fusion fragment according to the invention may comprise the region defined by nucleotides 1-121 of SEQ ID No: 1, which is required for pMEG1-1 activation by ZmMRP1, and the region defined by nucleotides 244-370 of SEQ ID No: 1, which contains a TATA box.

It is further possible to make a fusion of the region defined by nucleotides 1-121 of SEQ ID No: 1 (Meg1 promoter region) to any minimal promoter region (such as a –46 CaMV 35S promoter) in order to produce a promoter that is liable to be activated by ZmMRP1 and thus that is BETL-specific, the minimal promoter region being used to replace the region defined by nucleotides 244-370 from MEG1-1 promoter sequence (SEQ ID No: 1) in the fusion fragment defined above.

Such a result is also obtained using fragments 26 to 120 or 29 to 119 of SEQ ID No: 4.

A nucleic acid molecule "hybridizes" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989).

Such an hybridizing sequence has promoter activity specific to the endosperm according to the invention, preferentially specific to the BETL, and contains at least 15, 25, 35, 37, 50, 75, 100, 121, 122, 127, 150, 200, 220, 240, 250, 270, 300, 350, 360 or 365 nucleotides. Preferably, said hybridizing sequence may contain no more than 100 or 200 nucleotides.

The invention also encompasses modifications of the DNA sequences as depicted in SEQ ID No: 1 to 3 (pMEG1-1, pMEG1-2, pMEG1-3), or of sequence motifs thereof by, e.g., nucleotide replacements that do not affect the overall structure or binding motif of the nucleic acid molecule having promoter activity specific to the endosperm so that it remains capable of driving endosperm specific expression of a gene, and more particularly, a BETL specific expression of a gene.

"Homologous nucleic acid sequence", or "homologous DNA sequence", means any nucleic acid sequence which differs from any of the sequence SEQ ID No: 1 to 3 by a substitution, deletion and/or insertion of one or more nucleotides at positions such that these homologous nucleic acid sequences preserve the specificity property of promoters of sequences SEQ ID No: 1 to 3.

Preferably such a homologous nucleic acid sequence is at least 70% identical to one of the sequences SEQ ID No: 1 to 3, preferably at least 85% identical, more preferably at least 90, 91, 95, 98, 99.9% identical. Also preferably, the degree of identity is defined by comparison with the entire sequence of reference, SEQ ID No: 1, SEQ ID No: 2 or SEQ ID No: 3.

Homology is generally determined using a sequence analysis software (for example, the Sequence Analysis Software package of the Genetics Computer Group, University of Wisconsin Biotechnology Center, 1710 University Avenue, Madison, Wis. 53705). Similar nucleotide sequences are aligned in order to obtain the maximum degree of homology (i.e. identity). To this end, it may be necessary to artificially introduce gaps in the sequence. Once the optimum alignment has been achieved, the degree of homology (i.e. identity) is established by recording all the positions for which the nucleotides of the two compared sequences are identical, with respect to the total number of positions.

In a preferential manner such a homologous nucleic acid sequence specifically hybridizes to a sequence which is complementary to one of the sequences SEQ ID No: 1 to 3 under stringent conditions. The parameters defining the stringency conditions depend on the temperature at which 50% of the paired strands separate (Tm).

For sequences comprising more than 30 bases, Tm is defined by the equation: Tm=81.5+0.41 (% G+C)+16.6 Log (concentration in cations)−0.63 (% formamide)−(600/number of bases) (Sambrook et al., 1989).

For sequences shorter than 30 bases, Tm is defined by the equation: Tm=4(G+C)+2(A+T).

Under appropriate stringency conditions, in which non-specific (aspecific) sequences do not hybridize, the temperature of hybridization is approximately between 5 and 30° C., preferably between 5 and 10° C. below Tm and hybridization buffers used are preferably solutions of higher ionic force like a solution 6*SSC for example.

In addition, it is possible to derive essential, regulatory elements from the promoters provided herein. Thus, those elements of the promoter sequence responsible for both its function as a promoter and, more importantly, its endosperm specificity, particularly its BETL specificity, can be isolated and incorporated into nucleic acid molecules which, although not falling within the definitions (a) to (e) above, nonetheless still function in an equivalent manner.

The present invention also provides a recombinant or isolated nucleic acid molecule comprising, or consisting of, one or more regulatory elements derived from any one of the sequences (a) to (e) and which is capable of driving expression specifically in the endosperm, and preferably at an early stage of the development of the endosperm.

According to an embodiment of the invention, the nucleic acid molecule having promoter activity specific to the endosperm preferentially has a maternal parent-of-origin pattern of expression. As used herein, the term "maternal parent-of-origin pattern of expression" refers to the expression of a gene maternally imprinted. Imprinting is an epigenetic mechanism by which a particular allele is silenced according to its parental origin. This means that genes subjected to genomic imprinting have monoallelic expression, instead of biallelic expression as usual for autosomal genes, which is based on the sex of the transmitting parent.

The isolation of promoters that are regulated via imprinting provides an additional level of control compared to normal, non-imprinted promoters. Accordingly, the level of expression of a gene of interest can advantageously be controlled via the direction of the genetic cross between one plant carrying an imprinted transgene and the other plant lacking the transgene.

Preferably, the nucleic acid molecule having promoter activity specific to the endosperm which has a maternal parent-of-origin pattern of expression consists in SEQ ID No: 1.

SEQ ID No: 62 is also a nucleic acid molecule having promoter activity specific to the endosperm which has a maternal parent-of-origin pattern of expression, and is a part of the invention as any of SEQ ID No: 1 to 3.

The nucleic acid molecules having promoter activity specific to the endosperm according to the invention can be isolated from various plant species, notably Angiosperm plants, Monocotyledons or Dicotyledons and are preferably nucleic acid molecules isolated from a plant selected from the group consisting of maize, teosintes, rice, sorghum, wheat, barley, rye, pea, and sugar cane. Still preferably, the plant is maize.

It is possible for the person skilled in the art to isolate with the help of promoter sequences of the invention, corresponding genes from other species ("orthologous" genes).

This can be done by conventional techniques known in the art, for example, by using a promoter sequence depicted in any one of SEQ ID No: 1 to 3 as a hybridization probe or by designing appropriate PCR primers.

It is preferable to start with coding DNA sequences or Protein sequences via TBLASTN queries. The approach used to isolate rice Meg1 promoters, for example, is to use the Protein sequence of ZmMeg1-1, preferably the most conserved region identified via an alignment of all the Meg proteins, do a TBLASTN with this sequence against Rice ESTs, then use this EST to find the genomic sequence or directly use TBLASTN against the rice genome sequence. The same approach is used to isolate wheat Meg1 promoters.

It is then possible to isolate the corresponding promoter region by conventional techniques and test it for its expression pattern by known techniques (e.g. reporter gene analysis).

Another object of the present invention is a nucleotide construction, referred to as an expression cassette, comprising a nucleic acid molecule having promoter activity specific to the endosperm as defined above, operatively linked to at least one gene of interest.

"Operatively linked" refers to functional linkage between a nucleic acid molecule having promoter activity according to the invention and the gene of interest.

The gene of interest can be of a heterologous origin.

The gene of interest can be placed in the sense or antisense orientation.

According to an embodiment, the gene of interest may be selected from the group consisting of a sequence that encode a peptide or a protein, an antisense RNA sequence, a sense RNA sequence, both a sense and antisense RNA sequence and/or a ribozyme.

Preferentially, the gene of interest is a sequence that codes for a protein or for a peptide.

The said gene of interest can for example code for a protein involved in the development of the embryo and/or of the endosperm, the determination of seed size and/or quality (e.g. MRP1 or Ferretin (Lobreaux S. et al. 1992)), cell growth (proteins regulating cell division including cytokinin or auxin genes, e.g. ipt (Zhang et al. 1995), the flow of nutrients or nutrient transfer (transporters (Bolchi A. et al. 1999)), proteins involved in fatty acids metabolism. The gene of interest may also encode an enzyme involved in sugar metabolism such as invertases (e.g. incW2 (Taliercio E W et al. 1999)), sucrose synthases (e.g. Sh1), the saccharose phosphate synthase, saccharose synthase, UDP-Glucose pyrophosphorylase, ADP-glucose pyrophosphorylase (Thomas W. Greene et al. 1998), starch branching enzyme (Ming Gao et al. 1997) or the starch synthase (Mary E. Knight et al. 1998). The gene of interest could also code for a hexokinase as the one described by Jang et al. (1997) in order to improve grain filling. The gene of interest may additionally code for a protein that is involved in amino acids transfer, such as a methionine permease or a lysine permease, or a sulphur transporter etc. It can also code for a toxic protein such as Barnase, for a protein activating or inhibiting other genes, such as transcriptional regulators including transactivators modified to act as dominant activators or repressors of transcription (e.g. fusions to the engrailed domain (Poole et al., 1985) or co-repressors for example), or for a protein improving resistance to pathogens (e.g. BAP2, MRP1).

Preferably, said gene of interest encodes a protein selected from:

a protein whose specific expression in the endosperm, and particularly in the BETL, makes it possible to increase nutrient uptake and thus seed size and/or quality; examples of such a protein include an invertase like Incw2 or like Ivr1 (EP 0 442 592), a sucrose synthase like Sh1 (WO 02/067662) or any transporters of sugar and nitrogen or a MRP1 protein etc;

a protein that improves resistance to pathogens; examples of such a protein include a BAP Protein (Basal Layer Antifungal Protein) (Serna at al., 2001), or anti-fungal peptides, or a MRP1 protein or a protein that encodes an oxalate oxidase (WO 92/15685) or a protein that encodes a chitinase (WO 92/01792 or U.S. Pat. No. 5,446,138) or a protein that encodes a glucanase (WO 93/02197) etc.

A protein that "improves resistance to pathogens" or "a protein improving resistance to pathogens" means a protein that, when expressed in a plant or a part of a plant, confers or improves resistance to pathogens to said plant, or part thereof. Said transformed plant has a better resistance to pathogens than the non-transformed plant (wild-type).

The said gene of interest can also be associated with other regulating elements such as transcription termination sequences (terminators). By way of examples of such sequences, it is possible to cite the polyA 35S terminator of the cauliflower mosaic virus (CaMV), described in the article of Franck et al. (1980) and the NOS terminator corresponding to the region in the non-coding 3' region of the nopaline synthase gene of the Ti-plasmid of the *Agrobacterium tumefaciens* nopaline strain (Depicker et al. 1992).

Preferably, the terminator used is the 3'CaMV.

According to the invention, the expression cassette, comprising a nucleic acid molecule having promoter activity specific to the endosperm as defined above, operatively linked to at least one gene of interest may further comprise one or several selection marker genes for plants, useful for transformation and selection.

In the present invention, the term "selectable marker", "selectable gene", "selectable marker gene", "selection marker gene", "marker gene" are used interchangeably.

These selectable markers include, but are not limited to, antibiotic resistance genes, herbicide resistance genes or visible marker genes. Other phenotypic markers are known in the art and may be used in this invention.

A number of selective agents and resistance genes are known in the art. (See, for example, Hauptmann et al., 1988; Dekeyser et al., 1988; Eichholtz et al., 1987; and Meijer et al., 1991).

Notably the selectable marker used can be the bar gene conferring resistance to bialaphos (White et al., 1990), the sulfonamide herbicide Asulam resistance gene, sul (described in WO 98/49316) encoding a type I dihydropterate synthase (DHPS), the nptII gene conferring resistance to a group of antibiotics including kanamycin, G418, paromomycin and neomycin (Bevan et al., 1983), the hph gene conferring resistance to hygromycin (Gritz et al., 1983), the EPSPS gene conferring tolerance to glyphosate (U.S. Pat. No. 5,188, 642), the HPPD gene conferring resistance to isoxazoles (WO 96/38567), the gene encoding for the GUS enzyme, the green fluorescent protein (GFP), expression of which, confers a recognisible physical characteristic to transformed cells, the chloramphenicol transferase gene, expression of which, detoxifies chloramphenicol.

Advantageously, the selectable marker gene is inserted between a promoter and a terminator in a second expression cassette. Said second expression cassette being integrated in the same vector as the expression cassette containing the gene of interest under transcriptional control of a promoter according to the invention.

According to this advantageous embodiment, the marker gene is preferably controlled by a promoter which allows expression in cells, thus allowing selection of cells or tissue containing the marker at any stage of development of the plant. Preferred promoters are the promoter of nopaline synthase gene of *Agrobacterium*, the promoter derived from the gene which encodes the 35S subunit of cauliflower mosaic virus (CaMV) coat protein, and the rice actin promoter. However, any other suitable second promoter may be used.

Any terminator may be used. Preferred terminators are the 3'CaMV and Nos terminator as previously described.

Advantageously, the expression cassette containing the selectable marker gene is comprised between two Ds elements (transposons) in order for its removal at a later stage by interacting with the Ac transposase. This elimination system is described in Yoder et al. (1993).

For the transformation step, two vectors could be used, the first one comprising the expression cassette containing the gene of interest and the second one comprising the expression cassette containing the selectable marker gene. The same host cell being transformed with these two vectors (co-transformation).

The expression cassettes according to the invention may additionally contain transit peptide sequences. There are numerous examples in the art of transit peptides which may be used to deliver a target protein into a plastid organelle such as the small subunit (SSU) transit peptide of ribulose biphosphate carboxylase.

Other elements like introns and enhancers can also be present in the nucleic sequence of interest in order to improve the expression of the gene of interest.

Among useful introns, the first intron of maize adh1S can be placed between the promoter and the coding sequence. This intron when included in a gene construct increased the expression of the desired protein in maize cells (Callis et al., 1987). One also can use the $1^{st}$ intron of the shrunken 1 gene of the maize (Maas et al., 1991), the $1^{st}$ intron of the catalase gene of the bean catalase (CAT-1) (Ohta et al., 1990), the $2^{nd}$ intron of the ST-LS1 gene of potato (Vancanneyt et al. 1990), the DSV intron of the yellow dwarf virus of tobacco (Morris et al., 1992), the actin-1 intron (act-1) of rice (McElroy et al., 1990) and intron 1 of triosephosphate isomerase (TPI) (Snowdon et al., 1996). Preferentially, the intron used in the present invention is the Hsp70 intron or the Sh1 intron.

The expression cassettes may additionally contain 5' leader sequences. Such leader sequences can act to enhance translation. Such 5' leaders are known in the art and include, but are not limited to, picornavirus leaders, for example, the EMCV leader (Encephalomyocarditis 5' noncoding region) (Elroy-Stein, Fuerest, and Moss B., 1989); potyvirus leaders, for example, the TEV leader (Tobacco etch Virus) (Allison et al., 1986); the human immunoglobulin heavy-chain binding protein leader (BiP) (Macejack and Sarnow, 1991); the untranslated leader from the coat protein mRNA of alfalfa mosaic virus (AMV RNA 4) (Jobling and Gehrke, 1987) the tobacco mosaic virus leader (TMV) (Gallie et al., 1989); and the maize chlorotic mottle virus leader (MCMV) (Lommel et al., 1991). See also, Della-Cioppa et al. (1987). Other methods known to enhance translation can be utilized, for example introns, and the like.

Any expression cassette according to the invention, may further comprises a gene encoding a MRP1 protein, preferably the ZmMRP1 protein.

The ZmMRP1 protein is described in Gomez et al (2002). The nucleic acid sequence and amino acid sequence of ZmMRP1 are shown in SEQ ID No:51 and 52, respectively. However, any protein homologous to MRP1, and particularly to ZmMRP1, that have the same expression pattern can be used.

Such MRP1 protein can be used according to different ways:
  MRP1 as anti-fungal protein (resistance to pathogens) operatively linked to MEG1 promoter sequence SEQ ID No: 1 to 3, or a fragment thereof:
  A first expression cassette comprising an MRP1 protein or a fragment thereof, preferably the ZmMRP1 protein, operatively linked to a MEG1 promoter, preferably ZmMEG1-1 promoter, and to a terminator and a second expression cassette comprising a marker gene inserted between a promoter and a terminator; these two expression cassettes being inserted in the same vector for transformation or these two cassettes being inserted in two different vectors being co-transformed as previously described.
  MRP1 as transactivator for MEG1 promoter:
  A first expression cassette comprising a gene of interest, operatively linked to a MEG1 promoter, preferably ZmMEG1-1 promoter, and to a terminator; a second expression cassette comprising a MRP1 protein, preferably the ZmMRP1 protein inserted between a promoter and a terminator; a third expression cassette comprising a marker gene inserted between a promoter and a terminator; these three expression cassettes being inserted into the same vector for transformation or these three expression cassettes being inserted into three different vectors being co-transformed as previously described.

This second way of use is a binary system of expression, i.e. two plants are crossed, the first one with a gene of interest operatively linked to MEG1 promoter (preferably ZmMEG1-1) and the other with for example a leaf promoter linked to MRP1. The result is that in the hybrid the expression of the gene of interest is not only present in the BETL but also in the leaf.

In preparing the expression cassettes, the various DNA sequences or fragments may be manipulated, so as to provide DNA sequences or fragments in the proper orientation and, as appropriate, in the proper reading frame. Towards this end, adapters or linkers may be employed to join the DNA fragments and/or other manipulations may be required to provide convenient restriction sites, removal of superfluous DNA, removal of restriction sites, or the like. For this purpose, in vitro mutagenesis, primer repair, restriction, annealing, ligation, PCR, or the like may be employed, where nucleotide insertions, deletions or substitutions, for example transitions and transversions, may be involved. These techniques are well known by those skilled in the art.

Another object of the invention is any nucleotide vector referred to as an expression vector, such as a plasmid, which can be used for transforming host cells, characterized in that it contains at least an expression cassette as defined above. The construction of expression vectors for the transformation is within the capability of one skilled in the art following standard techniques.

The decision as to whether to use a vector, or which vector to use, is guided by the method of transformation selected, and by the host cell selected.

Where a naked nucleic acid introduction method is used, then the vector can be the minimal nucleic acid sequences necessary to confer the desired phenotype, without the need for additional sequences.

Possible vectors include the Ti plasmid vectors, shuttle vectors designed merely to maximally yield high numbers of copies, episomal vectors containing minimal sequences necessary for ultimate replication once transformation has occured, transposon vectors, including the possibility of RNA forms of the gene sequences. The selection of vectors and methods to construct them are commonly known to persons of ordinary skill in the art and are described in general technical references (Mullis, K B (1987), *Methods in Enzymology*).

For other transformation methods requiring a vector, selection of an appropriate vector is relatively simple, as the constraints are minimal. The apparent minimal traits of the vector are that the desired nucleic acid sequence be introduced in a relatively intact state. Thus, any vector which produces a plant carrying the introduced DNA sequence should be sufficient. Also, any vector which introduces a substantially intact RNA which can ultimately be converted into a stably maintained DNA sequence should be acceptable.

However, any additional attached vector sequences which confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenic plants.

The vector can exist, for example, in the form of a phage, a plasmid or a cosmid. The construction of such expression vectors for transformation is well known in the art and uses standard techniques. Mention may be made of the methods described by Sambrook et al. (1989).

Another object of the invention is a host cell, containing at least an expression vector as described above.

The decision as to whether to use a host cell, or which host cell to use, is guided by the method of transformation.

The host cell can be any prokaryotic or eukaryotic cell. Any of a large number of available and well-known host cells may be used in the practice of this invention. The selection of a particular host is dependent upon a number of factors recognized by the art. These include, for example, compatibility with the chosen expression vector, bio-safety and costs. Useful hosts include bacteria such as *E. coli* sp. or *Agrobacterium*. A plant host cell, may be also used, notably an Angiosperm plant cell, Monocotyledon as Dicotyledon plant cell, particularly a cereal or oily plant cell, selected in particular from the group consisting of maize, wheat, barley, rice, rape and sunflower, preferentially maize.

More particularly, the host cell used in carrying out the invention is *Agrobacterium tumefaciens*, according to the method described in the article of An et al., 1986, or *Agrobacterium rhizogenes*, according to the method described in the article of Jouanin et al., 1987.

The invention also concerns a transgenic plant or part of a transgenic plant, in particular fruit, seed, grain or pollen, comprising such a cell or generated from such a cell. Where the plant contains endogenously a MEG1 promoter or gene according to the invention, it will be understood that the transgenic plant according to the invention comprises an additional "exogenous" gene MEG1 gene or promoter, for instance integrated by transgenese.

A whole plant can be regenerated from a single transformed plant cell. Thus, in a further aspect the present invention provides transgenic plants (or parts of them) including nucleic acid sequences in accordance with the invention. The regeneration can proceed by known methods.

The seeds which grow, by fertilization, from this plant also contain this transgene in their genome.

Advantageously, the transgenic plant obtained can produce grains with a larger endosperm in comparison with a non-transformed plant, particularly grains with starch, oil contents or protein contents which are modified in comparison with a non-transformed plant.

A plant or part of a plant according to the invention could be a plant or a part of it from various species, notably an Angiosperm, Monocotyledons as Dicotyledons, preferably a cereal or oily plant, selected in particular from the group consisting of maize, rice, wheat, barley, rape and sunflower, preferentially maize.

As used herein, the term "oily plant" denotes a plant that is capable of producing oil, and preferably that is cultivated for oil production.

The hybrid plants obtained by crossing plants according to the invention also form part of the invention.

An other object of the invention is a method of obtaining a plant having improved agronomic qualities and/or improved resistance to pathogen, comprising the steps consisting of:
(a) transforming at least one plant cell by means of a at least a vector as defined previously;
(b) cultivating the cell(s) thus transformed so as to generate a plant containing in its genome at least an expression cassette according to the invention, whereby said plant has improved agronomic qualities and/or improved resistance to pathogen.

According to the invention, "improved agronomic qualities" means improved agronomic qualities and/or improved nutritional qualities, notably yield, food or industrial qualities of a plant or a part thereof. Seed size, yield, seed number, seed composition are considered as elements conferring improved agronomic qualities to a plant as compared to a non-transformed plant (wild-type).

According to the invention, "improved resistance to pathogens" means that the transformed plant have a better resistance to pathogens than the non-transformed plant (wild-type).

The transformation of vegetable cells can be achieved by any one of the techniques known to one skilled in the art.

It is possible to cite in particular the methods of direct transfer of genes such as direct micro-injection into plant embryoids (Neuhaus et coll. 1997), vacuum infiltration (Bechtold at al. 1993) or electroporation (Chupeau et coll., 1989) or direct precipitation by means of PEG (Schocher et coll., 1986) or the bombardment by gun of particules covered with the plasmidic DNA of interest (Fromm M et al., 1990).

It is also possible to infect the plant with a bacterial strain, in particular *Agrobacterium*. According to one embodiment of the method of the invention, the vegetable cells are transformed by a vector according to the invention, the said cell host being able to infect the said vegetable cells by allowing the integration, in the genome of the latter, of the nucleotide sequences of interest initially contained in the above-mentioned vector genome. Advantageously, the above-mentioned cell host used is *Agrobacterium tumefaciens*, in particular according to the method described in the article by An et al., (1986), or *Agrobacterium rhizogene*, in particular according to the method described in the article by Guerche et al. (1987).

For example, the transformation of vegetable cells can be achieved by the transfer of the T region of the tumour-inducing extra-chromosome circular plasmid of *Agrobacterium tumefaciens*, using a binary system (Watson et al., 1994). To do this, two vectors are constructed. In one of these vectors the T region has been eliminated by deletion, with exception of the right and left borders, a marker gene being inserted between them to allow selection in the plant cells. The other partner of the binary system is an auxiliary plasmid Ti, a modified plasmid which no longer has any T region but still contains the virulence genes vir necessary to the transformation of the vegetable cell.

According to a preferred mode, it is possible to use the method described by Ishida et al. (1996) for the transformation of Monocotyledons.

According to another protocol, the transformation is achieved according to the method described by Finer et al. (1992) using the tungsten or gold particle gun.

Selection:

The engineered plant material may be selected or screened for transformants (those that have incorporated or integrated the introduced nucleotide construction(s)). Such selection and screening methodologies are well known to those skilled in the art. The selection and screening method is chosen depending on the marker gene used.

An isolated transformant may then be regenerated into a plant.

Regeneration:

Normally, regeneration is involved in obtaining a whole plant from the transformation process. The term "regeneration" as used herein, means growing a whole plant cell, a group of plant cells, a plant part or a plant piece (for example, from a protoplast, callus, or tissue part).

Methods of regenerating whole plants from plant cells are known in the art, and the method of obtaining transformed and regenerated plants is not critical to this invention.

In general, transformed plant cells are cultured in an appropriate medium, which may contain selective agents such as antibiotics, where selectable markers are used to facilitate identification, of transformed plant cells. Once callus forms, shoot formation can be encouraged by employing appropriate plant hormones in accordance with known methods and shoots transferred to rooting medium for regeneration of plants. The plants may then be used to establish repetitive generations, either from seeds or using vegetative propagation techniques.

The invention further relates to the use of at least an expression cassette as previously defined, for obtaining a transgenic plant exhibiting improved agronomic qualities and/or improved resistance to pathogen.

The agronomic quality of a plant is improved by acting in particular on the size of the embryo or of the endosperm and/or its development.

This is because an early specific action on the development of the tissues of the embryo and of the endosperm can be sought: according to the relative size of one or other it would be possible to obtain seeds or fruits with a higher starch (large endosperm) and/or oil (large embryo) content, via the use respectively of stimulator genes (hormone of the cellular cycle for example) or inhibitor genes (toxic protein or transcription inhibitor for example). A reduction in BETL size would create a miniature type seed which could have a reduced endosperm/embryo ratio. The most likely effect of increasing BETL activity/size would be to increase endosperm size. This may translate into a bigger embryo also.

By way of example, the use of genes coding for hormones (cytokinins, auxins) under the control of the promoters described according to the invention, would make it possible to modify the process of cellularisation and thus the development of the endosperm.

An effect on the accumulation of nutrients in the embryo and endosperm can also be sought, by using for example, as genes of interest, genes coding for transporters of nutrients (sugar in particular), or genes coding for inhibitors of these transporters, leading to differential accumulation of nutrients in the endosperm or embryo.

The invention also concerns the use of the transgenic plants obtained according to the invention, or parts of these plants, in particular seeds, grains, and fruits for preparing derived products, in particular food products.

The invention relates to seeds obtained from a plant transformed with a nucleic acid sequence according to the invention (SEQ ID No: 1-4, 5, 7, 9, 11, 13, 15 and 58).

The products obtained, whether it be seeds with a higher oil content, flours of seeds or grains with a higher starch, protein or oil content, also come within the scope of the invention.

The invention also provides any composition for human or animal food prepared from the said obtained products.

The invention further provides an isolated nucleic acid molecule encoding a plant basal endosperm transfer cell layer (BETL) protein, which comprises a sequence selected from the group consisting of:
 (a) a nucleotide sequence encoding a protein consisting of an amino acid sequence as depicted in SEQ ID No: 6, 8, 10, 53, 12, 14 or 16 (ZmMEG1-1, ZmMEG1-2, ZmMEG1-3 (first and second ORF), ZmMEG1-4, ZmMEG1-5, and ZmMEG1-6, respectively) and variants thereof;
 (b) a nucleotide sequence as depicted in SEQ ID No: 5, 7, 9, 11, 13, 15, or 58 (cDNA of ZmMEG1-1, ZmMEG1-2, ZmMEG1-3, ZmMEG1-4, ZmMEG1-5, and ZmMEG1-6, and genomic sequence of ZmMEG1-1, respectively);
 (c) a nucleotide sequence hybridizing under stringent conditions with the complementary strand of a nucleic acid molecule as defined in (a) or (b);
 (d) a sequence encoding a fragment of a protein encoded by a sequence as defined in any one of (a) to (c).

Preferably, the protein encoded by the nucleic acid molecule according to the invention is specific to the BETL.

"Specific to the BETL" means, as used in the present invention, that the protein is expressed predominantly in the BETL, and more particularly, exclusively in the BETL.

Preferentially, the amino acid sequence encoded by a nucleotide sequence according consists in SEQ ID No: 6.

Also preferably, the sequence encoding a fragment of a BETL protein according to the invention comprises a nucleic acid sequence encoding the PCKDNKCYCCIGGRTH sequence (SEQ ID No:54). This fragment was found to be conserved among all maize MEG1 proteins (ZmMEG1-1, ZmMEG1-2, ZmMEG1-3 (first and second ORF), ZmMEG1-4, ZmMEG1-5, and ZmMEG1-6) but also in related proteins from barley and wheat.

Preferentially, the nucleic acid molecules comprising a nucleotide sequence according to the invention consists in any one of SEQ ID No: 5, 7, 9, 11, 13 or 15, more preferentially consists in SEQ ID No: 5. Additionally said nucleic acid molecules may comprise the genomic sequence of Zm MEG1-1 shown in SEQ ID No: 58.

As used herein "variants" means that the sequence differs in one or more positions in comparison with these sequences SEQ ID No: 6, 8, 10, 53, 12, 14 or 16 as long as they encode a protein expressed in the BETL.

Such molecules comprise those which are variants of the BETL protein according to the invention and differ, for example, by way of amino acid and/or nucleotide deletion(s), insertion(s), substitution(s), addition(s) and/or recombination(s) or any other modification(s) known in the art either alone or in combination from the above described amino acid sequences or their underlying nucleotide sequence(s). Methods for introducing such modifications in the nucleic acid molecules according to the invention are well-known to the person skilled in the art. The invention also relates to nucleic acid molecules the sequence of which differs from the nucleotide sequence of any of the above-described nucleic acid molecules due to the degeneracy of the genetic code.

The invention further relates to a protein encoded by said nucleic acid molecules. More specifically, the invention provides a plant basal endosperm transfer cell layer (BETL) protein or an biologically active fragment thereof encoded by a nucleic acid molecule as defined above. Preferably, a protein according to the invention may comprise, or consist in, an amino acid sequence selected from the group consisting of SEQ ID No: 6, 8, 10, 53, 12, 14 and 16. Still preferably said protein comprises, or consists in, SEQ ID No:6. Additionally, a preferred BETL protein comprises amino acid sequence shown in SEQ ID No: 54.

The proteins encoded by the various variants of the above-described nucleic acid molecules share specific common characteristics, such as biological activity, molecular weight, conformation, etc., as well as physical properties, such as electrophoretic mobility, chromatographic behavior, sedimentation coefficients, pH optimum, temperature optimum, stability, solubility, spectroscopic properties, etc.

Hybridization stringent conditions are defined as described above.

A "fragment" of a BETL protein or a nucleic acid molecule means a sequence, nucleotide sequence or amino acid sequence, which has a reduced length with regard to the nucleotide sequence or amino acid sequence of reference.

A preferred BETL protein fragment according to the invention comprises, or consists in, the amino acid sequence PCKDNKCYCCIGGRTH (SEQ ID No:54).

All such fragments and variants of the protein of the invention are included within the scope of the present invention, as long as the essential characteristic biological properties remain unaffected in kind, that is the novel nucleic acid molecules of the invention include all nucleotide sequences encoding proteins or peptides which have at least a part of the primary structural conformation for one or more epitopes capable of reacting with antibodies to BETL proteins which are encodable by a nucleic acid molecule as set forth above.

The nucleic acid molecule encoding a plant basal endosperm transfer cell layer (BETL) protein according to the invention can be isolated from various plant species, notably Angiosperm plants, Monocotyledons as Dicotyledons and are preferably nucleic acid molecules isolated from a plant selected from the group consisting of maize, teosintes, wheat, barley, rye, pea, rice, sorghum, and sugar cane. Preferably said plant is maize.

Another object of the present invention is a nucleotide construction, referred to as an expression cassette, comprising a nucleic acid molecule encoding a plant basal endosperm transfer cell layer (BETL) protein according to the invention, operatively linked to regulatory elements allowing the expression in prokaryotic and/or eukaryotic host cells. Regulatory elements are notably 5' and 3' regulatory sequences.

"Operatively linked" refers to functional linkage between the 5' and 3' regulatory sequences and the controlled nucleic acid sequence.

The 5' regulatory sequences are notably promoters.

Any suitable promoter could be used. It could be for example a tissue-specific promoter such as a root-specific promoter, a leaf-specific promoter, a seed-specific, etc. Numerous tissue-specific promoters are described in the literature and any one of them can be used. Preferably, the promoter is a pathogen inducible promoter. Such promoters include those from pathogenesis-related protein, which are induced following infection by a pathogen, e.g., PR proteins, SAR proteins, beta-1,3 glucanase, chitinase, etc.

Examples of promoters useful for plant transformation include the 35S promoter or the 19S promoter (Kay et al., 1987), the pCRV promoter (Depigny-This et al., 1992), the ubiquitin 1 promoter of maize (Christensen et al., 1996), the regulatory sequences of the T-DNA of *Agrobacterium tumefaciens*, including mannopine synthase, nopaline synthase, octopine synthase, the promoters regulated during seed development such as the HMWG promoter (High Molecular Weight Glutenin) of wheat (Anderson O. D. et al., 1989, Roberts et al., 1989), the waxy, zein or bronze promoters of maize, a promoter that is inducible by pathogens. The promoter may be a promoter as depicted in any of SEQ ID No: 1 to 3.

Preferentially, the promoter used is a pathogen inducible promoter or alternatively a constitutive promoter used to control the desired level of disease control (resistance to pathogen) in the plant.

The 3' regulatory sequence is notably terminators.

Among the terminators useful for plant transformation within the framework of the present invention, the ones which can be used are the polyA 35S terminator of the cauliflower mosaic virus (CaMV), described in the article of Franck et al. (1980), the NOS terminator corresponding to the region in the non coding 3' region of the nopaline synthase gene of the Ti-plasmid of *Agrobacterium tumefaciens* nopaline strain (Depicker et al. 1992), the histone terminator (EP 0 633 317), and the tml terminator.

Preferentially the terminator is the 3'Nos or 3'CaMV terminator.

Any other element, as previously described (intron, enhancer, transit peptide, . . . ) may be comprised in the expression cassette.

According to the invention, the expression cassette, comprising a nucleic acid molecule encoding a plant basal endosperm transfer cell layer (BETL) protein as defined above, operatively linked to regulatory elements may further comprises one or several selection marker gene for plants, useful for transformation and selection.

The selectable marker genes useful have been described previously.

Another object of the invention is any nucleotide vector referred to as an expression vector, such as a plasmid, which can be used for transforming host cells, characterized in that it contains at least an expression cassette comprising a nucleic acid molecule encoding a plant basal endosperm transfer cell layer (BETL) protein, as defined above.

Examples of useful expression vector have been described above.

Another object of the invention is a host cell, containing at least an expression vector as described above.

Examples of useful host cells have been described above.

The invention also relates to a transgenic plant, or a part of a transgenic plant (leaves, plant cell, plant tissue, grain, fruit, seed, . . . ) comprising a cell as described, notably comprising stably integrated into the genome a nucleic acid molecule encoding a plant basal endosperm transfer cell layer (BETL) protein, operatively linked to regulatory elements allowing transcription and/or expression of the nucleic acid molecule in plant cells.

A plant or part of a plant (plant cell, plant tissue, grain, seed, leaves, . . . ) according to the invention could be a plant or a part of it from various species, notably an Angiosperm, Monocotyledons or Dicotyledons, preferably a cereal or oily plant, selected in particular from the group consisting of maize, rice, wheat, barley, rape, and sunflower, preferentially maize.

In yet another aspect, the invention also relates to harvestable parts and to propagation material of the transgenic plants according to the invention which either contain transgenic plant cells expressing a nucleic acid molecule according to the invention or which contain cells which show a reduced level of the described protein. Harvestable parts can be in principle any useful parts of a plant, for example, leaves, stems, fruit, seeds, roots etc. Propagation material includes, for example, seeds, fruits, cuttings, seedlings, tubers, rootstocks etc.

The invention further relates to a plant basal endosperm transfer cell layer (BETL) protein or an immunologically or biologically active fragment thereof encodable by a nucleic acid molecule according to the invention.

The invention also relates to an antibody specifically recognizing a BETL protein according to the invention or a fragment, such as SEQ ID No: 54, or epitope thereof.

These antibodies can be monoclonal antibodies, polyclonal antibodies or synthetic antibodies as well as fragments of antibodies, such as Fab, Fv or scFv fragments etc. Techniques for producing such antibodies are classical methods well known by the one skilled in the art.

Another object of the invention is a method for improving plant pathogen resistance, comprising the steps consisting of:
a) transforming at least a plant cell by means of at least a vector as defined previously;
b) cultivating the cell(s) thus transformed so as to generate a plant containing in its genome at least an expression cassette according to the invention, whereby a plant with improved pathogen resistance is obtained.

Pathogens of the invention include, but are not limited to, viruses or viroids, bacteria, insects, nematodes, fungi, and the like. For example, *Fusarium* species (notably *Fusarium moniliforme, Fusarium graminearum*), *Sclerotinia sclerotiorum, Phoma*, Corn root worm, *Aphis gossypii*, etc. For maize, this would include especially ear mold fungal pathogens, such as *Fusarium monoliforme*.

Biological activity of the BETL proteins according to the invention can be assayed by any method known in the art. Assays to measure for example antimicrobial activity and the developmental pathways and defense responses that are influenced by the BETL protein are well known in the art.

Assays that measure antipathogenic activity (resistance to pathogen activity) are commonly known in the art, as are methods to quantitate disease resistance in plants following pathogen infection. Such techniques notably include, measuring over time, the average lesion diameter, the pathogen biomass, and the overall percentage of decayed plant tissues.

Antimicrobial and antipathogenic compositions are also included in the scope of the invention. The compositions of the present invention can be in a form suitable for direct application to the plant in need thereof or as a concentrate of a primary composition, which requires dilution with a suitable quantity of water or other diluent before application.

Additionally, the compositions can be used in formulations used for their antimicrobial and antipathogenic activities (resistance to pathogens). The proteins of the invention can be formulated with an acceptable carrier into a pesticidal composition(s) for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

The methodologies for transformation, selection, regeneration, are known to one skilled in the art and have been previously described.

Another object of the invention is a method for improving the agronomic quality of a plant, comprising the steps consisting of:
a) transforming at least a plant cell by means of at least a vector as defined previously;
b) cultivating the cell(s) thus transformed so as to generate a plant containing in its genome at least an expression cassette according to the invention, whereby a plant with improved agronomic quality is obtained.

More particularly, said plant exhibits an increased seed size as improved agronomic quality.

The overexpression of MEG1 protein into a plant result in a increased seed size. When overexpressing MEG1 protein, any promoter could be used in the expression cassette.

Preferably the promoter is chosen amongst a BETL specific promoter such as any one of the promoters according to the present invention, or the BETL2 promoter (WO 99/50427).

Moreover, the present invention relates to a kit comprising at least one of the aforementioned nucleic acid molecules, probes, conserved sequences, vectors, proteins, compositions or antibodies of the invention. The kit, or its components, according to the invention can be used in plant cell and plant tissue cultures, for example to detect expression levels of the transgene. The kit and its application are particularly useful to screen for antipathogenic effects in fungal cultures. The kit of the invention and its components are expected to be very useful in breeding new varieties of, for example, plants which display improved properties such as nutritional value or disease resistance (resistance to pathogens).

The present invention will be further understood in view of the annexed figures and following examples.

FIG. 1 is an autoradiograph of an AMD gel showing a maternal pattern of expression for ZmMEG1-1 (arrows). 1, F2 selfed; 2, Mo17 selfed; 3, F2 x Mo17; 4, Mo17 x F2; 5, A69Y selfed; 6, F2 selfed; 7, F2 x A69Y; 8, A69Y x F2.

Figure 2:
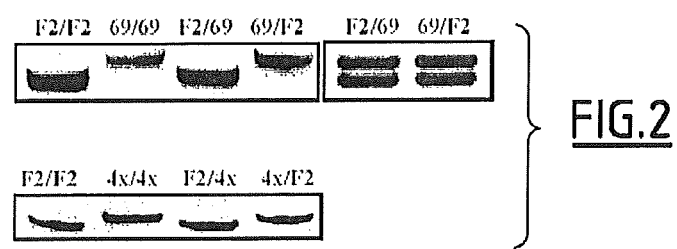

FIG. 2 depicts an allele-specific RT-PCR analysis of ZmMEG1-1 in the endosperm. Top, ZmMEG1-1 maternal allele is monoallelic at 4 DAP (single band) and biallelic at 12 DAP (double band). Bottom, monoallelic expression of Meg1 in interploidy crosses at 4 DAP. The parental inbred lines used were F2, A69Y (69) and tetraploid W23 (4x).

Figure 3:
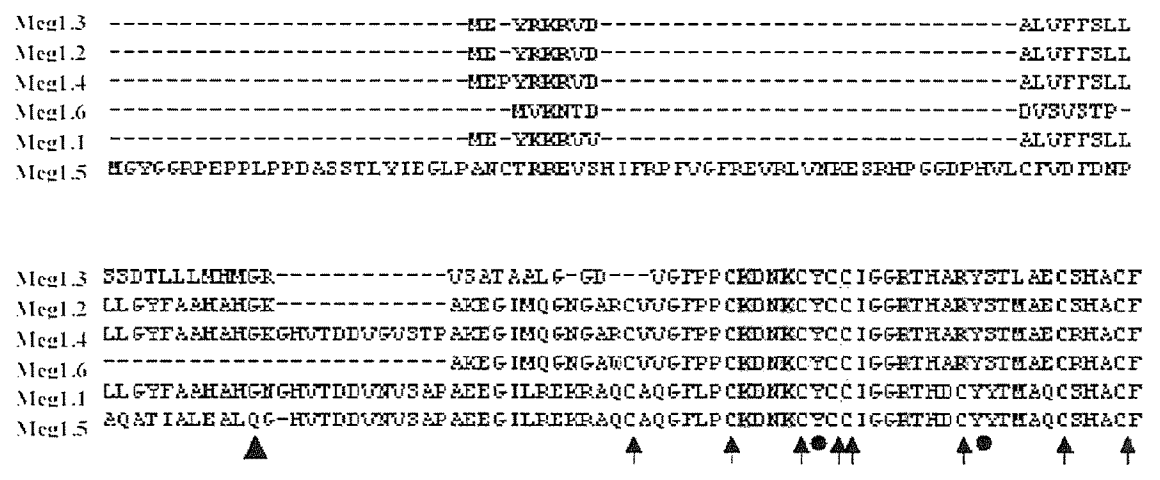

FIG. 3 represents the amino acid alignment of putative proteins with a ZmMEG1-1 domain. Arrows indicate the position of conserved cysteines and a circle indicates the position of conserved tyrosines putatively involved in the anchoring to the cell wall. In FIG. 3, Meg1.1 is SEQ ID NO: 6., Meg1.2 is SEQ ID NO: 8., Meg1.3 is SEQ ID NO: 10; Meg1.4 is SEQ ID NO: 12; Meg1.5 is SEQ ID NO: 14; and Meg1.6 is SEQ ID NO: 16.

FIGS. 4 to 7 represent ZmMEG1-1 protein characterization, and expression analysis of ZmMEG1-1 and five related cDNAs.

Figure 4:
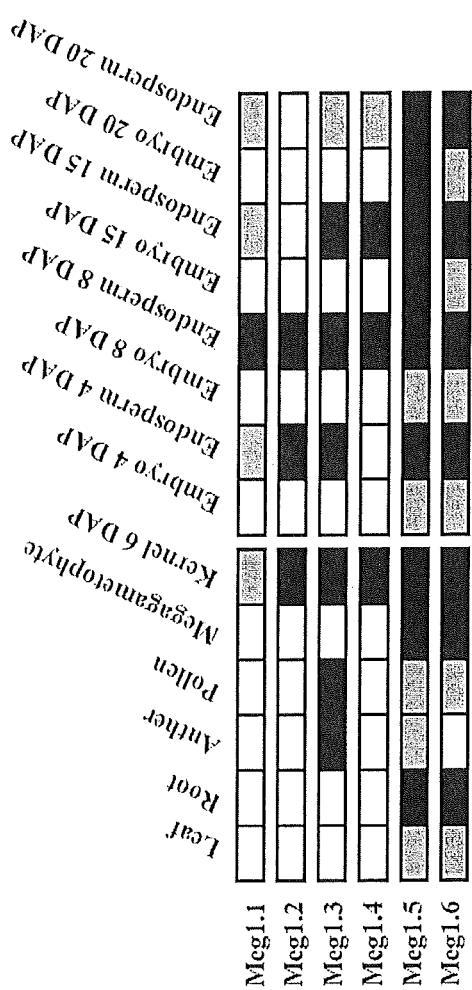

FIG. 4: RT-PCR analysis was carried out with different RNA samples isolated from a range of tissues and amplified with gene specific primers (see oligonucleotide table 1). Dark and light box coloration indicate high and intermediate signal respectively, and a white box indicates absence of signal.

Figure 5:
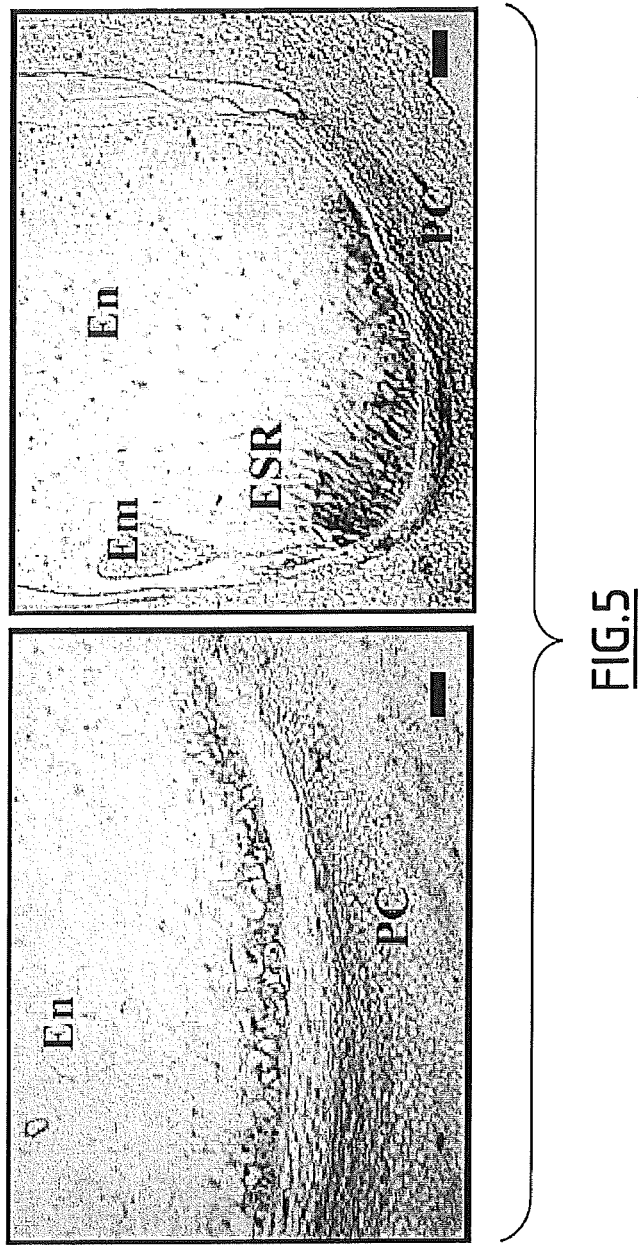

FIG. 5 depicts the In situ hybridization analysis of ZmMEG1-1 in developing seeds. Left, 4 DAP; Right 12 DAP.

Figure 6:
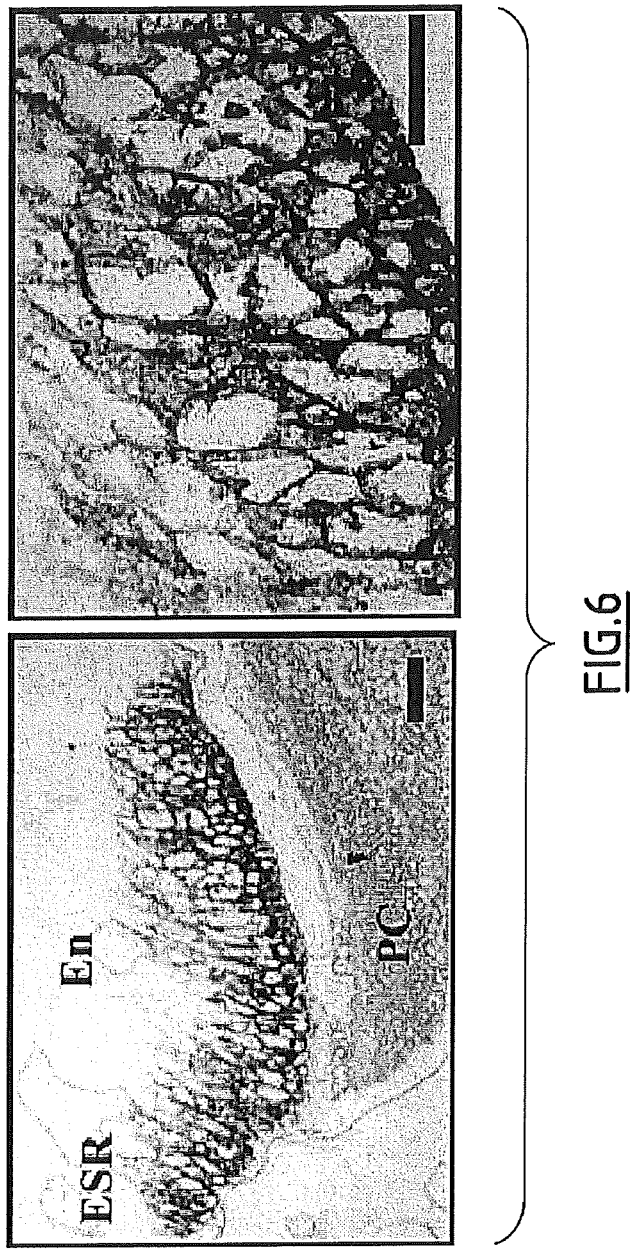

FIG. 6 shows Immunolocalization of ZmMEG1-1 protein. Left, 12 DAP BETL region; Right, cell wall localization of ZmMEG1-1 in BETL cells.

Figure 7:
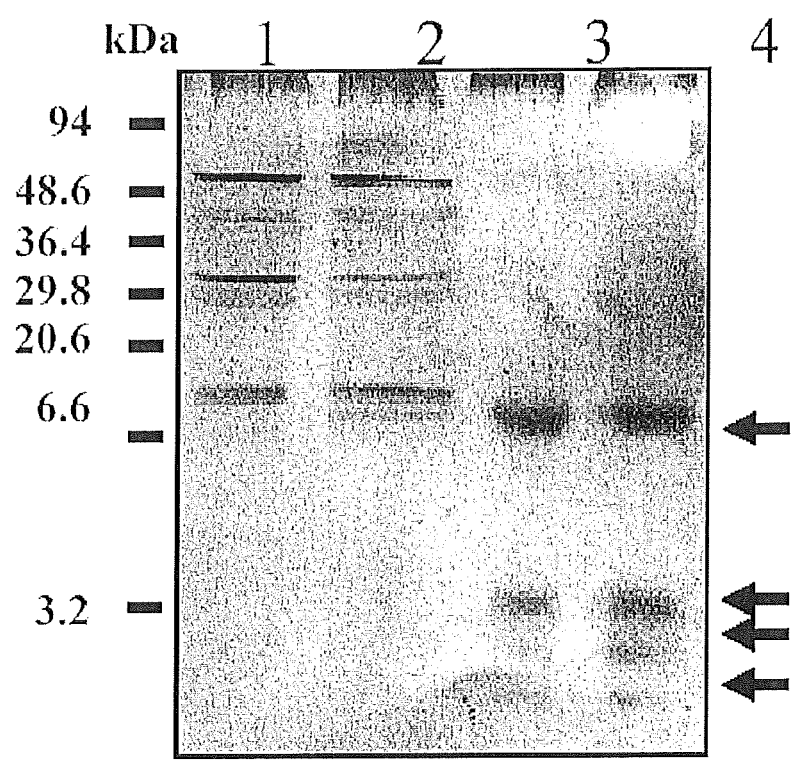

FIG. 7 is a Western analysis of proteins isolated from 10 DAP endosperms after subcellular fractionation.

1, cytoplasmic fraction I; 2, cytoplasmic fraction II; 3, cell wall fraction I; 4, cell wall fraction II. Arrows indicate the presence of different ZmMEG1-1 proteins. Em, embryo; En, endosperm; ESR, embryo surrounding region; PC, pedicel.

Figure 8:
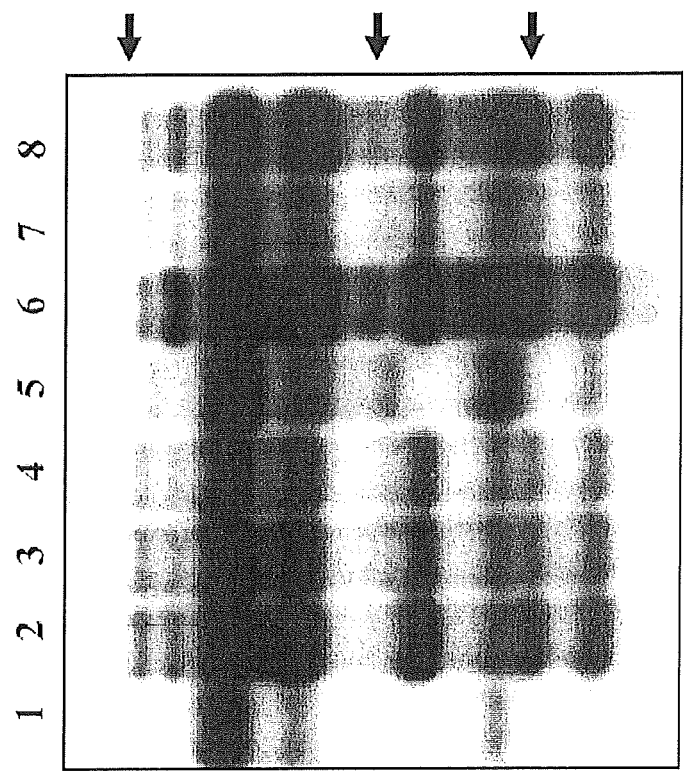

FIG. 8 indicates that ZmMEG1-1 is a member of a small gene family of which parental alleles are differentially methylated in the endosperm ZmMEG1-1 methylation analysis in embryo (1-4) and endosperm (5-8) at 6 DAP.

1, W22 self; 2, A69Y self; 3, W22 x A69Y; 4, A69Y x W22; 5, W22 self; 6, A69Y self; 7, W22 x A69Y; 8, A69Y x W22. Arrows indicate the presence of differentially methylated genomic fragments in the endosperm detected with a ZmMEG1-1 gene specific probe.

Figure 9:
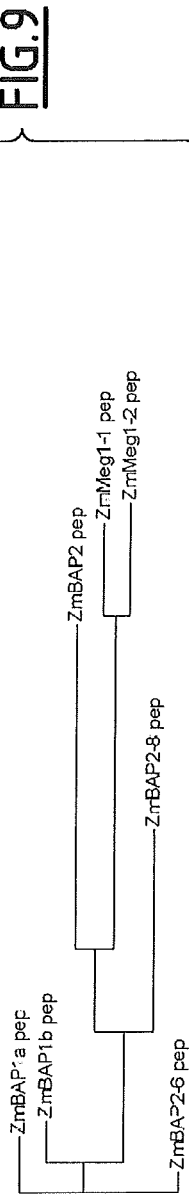

FIG. 9 represents the result of a sequence alignment of ZmMeg1-1 and ZmMeg1-2 with BAP proteins. In FIG. 9, ZmBAP1a pep is SEQ ID NO: 65; ZMBAP1b pep is SEQ ID NO: 66; ZmBAP2 pep is SEQ ID NO: 67; ZmBAP2-6 pep is SEQ ID NO: 68; ZmBAP2-8 pep is SEQ ID NO: 69; ZmMeg1-1 pep is SEQ ID NO: 6; ZmMeg1-2 pep is SEQ ID NO: 8; and the Consensus sequence is SEQ ID NO: 70.

Figure 10:
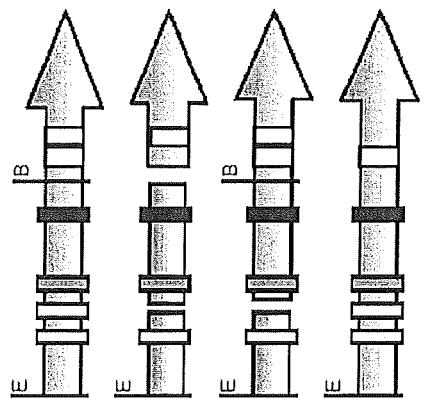

FIG. 10 represents analysis of the ZmMEG1-1 promoter region (SEQ ID NO: 1). Left, a minimal promoter sequence of ZmMEG1-1 is conserved amongst several ZmMEG1-1 promoters from the F2 inbred line. Right, these promoters showed high conservation of the four regions also present in other BETL-specific genes (named box I to IV). White boxes, putative TATA motifs; boxes I to IV are the conserved sequences amongst promoter regions of several known BETL-specific genes.

Figure 11:
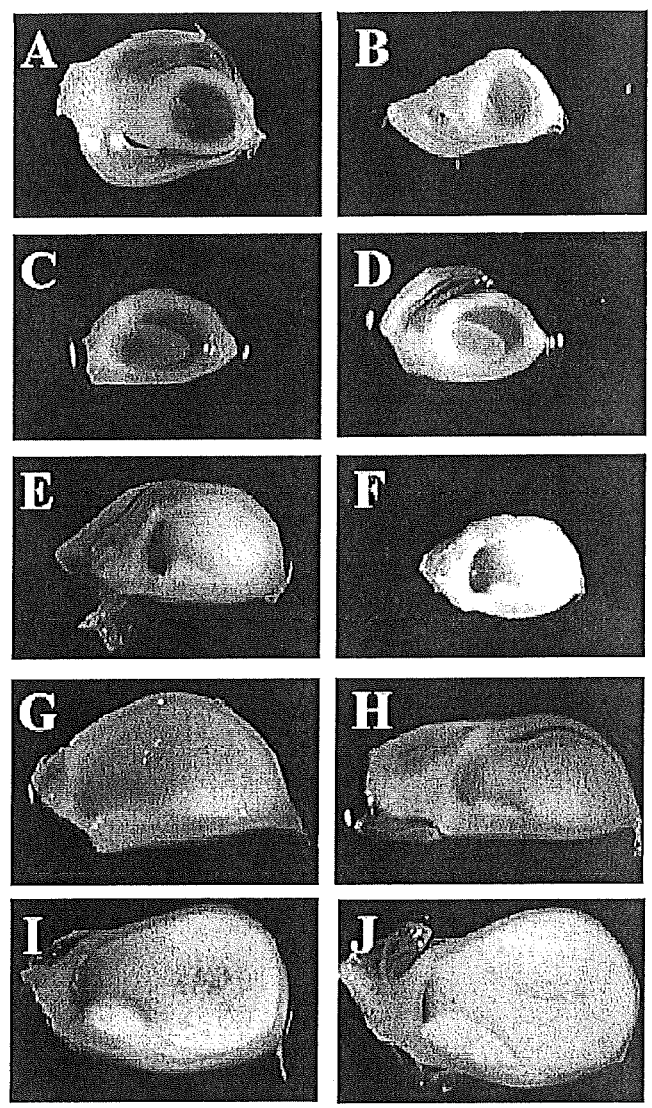

FIG. 11 represents the differential expression of pZm-MEG1-1:GUS in maize endosperm when inherited maternally and paternally. (A-J) sagittal sections of kernels stained for the GUS reporter, where (A, C, E, G and I) are seeds from an A188::pZmMEG1-1:GUS x A188 cross; (B, D, F, H and J) are seeds from the reciprocal A188 x A188::pZmMEG1-1:GUS cross. Note the presence of GUS signal in (A) and (C) at early stages of endosperm development but absent when paternally transmitted (B and D). (A and B) 4 DAP; (C and D) 6 DAP; (E and F) 10 DAP; (G and H) 15 DAP; (I and J) 20 DAP.

Figure 12:
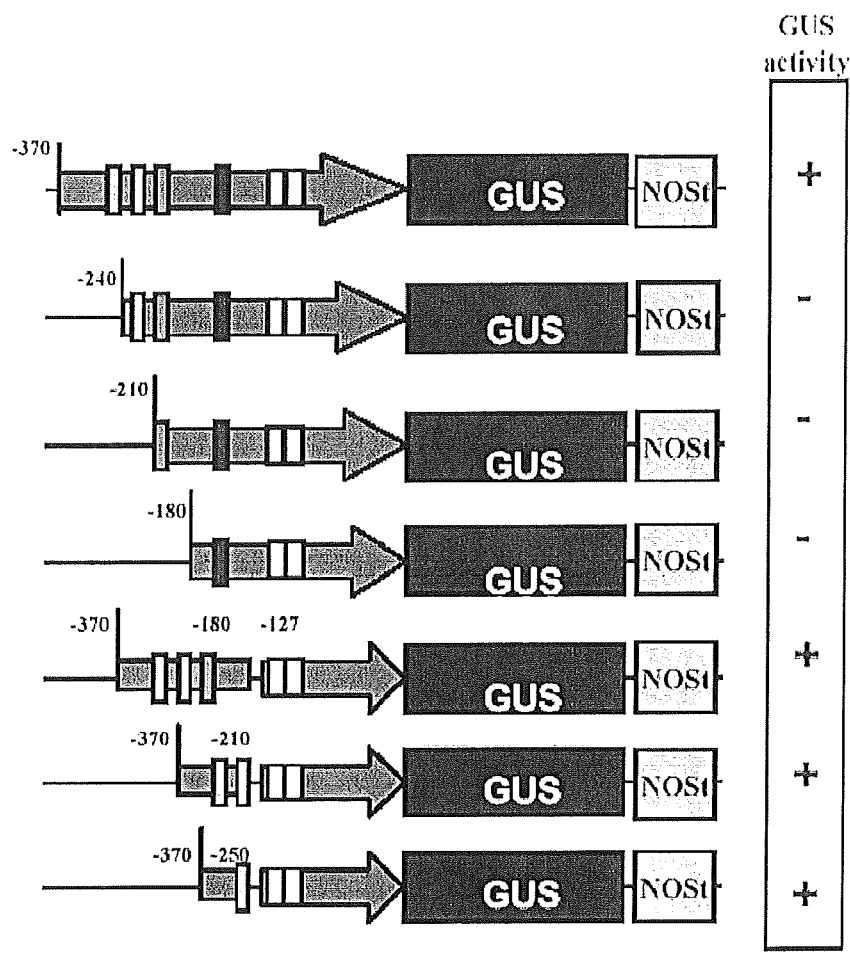

FIG. 12 is an analysis of the minimal promoter region of ZmMEG1-1. Left, Schematic representation of the promoter-deletion constructs employed in a co-bombardement experiment with a p35S:MRP1 construct. Right, results obtained from the co-bombardment assay. Plus signs indicate the presence of GUS staining (transactivation); Minus signs denote absence of GUS staining (lack of transactivation).

Figure 13:
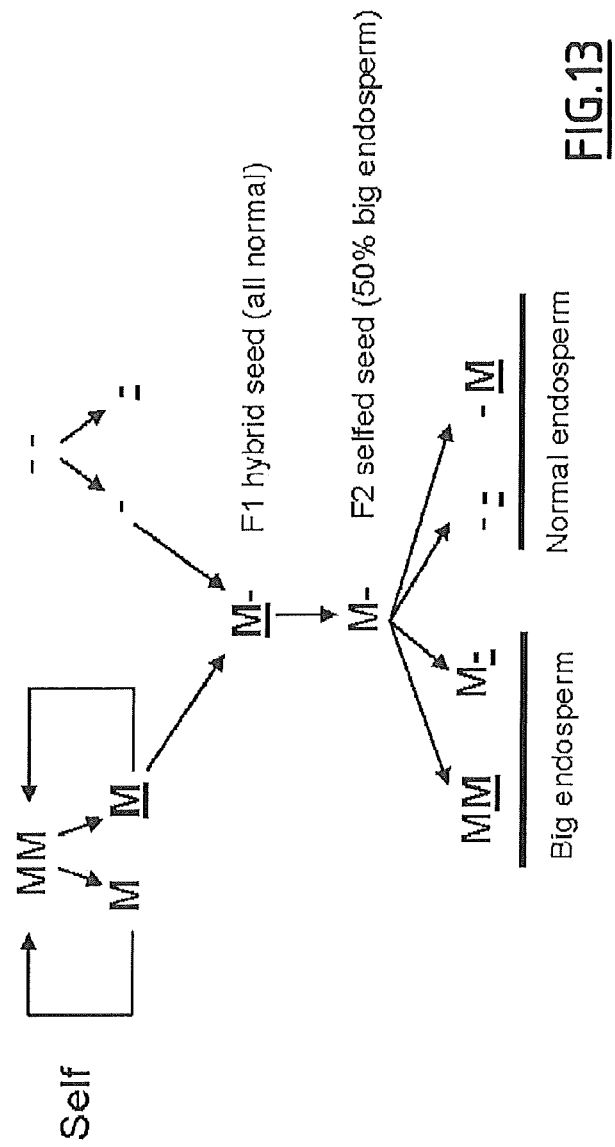

FIG. 13 is a diagrammatic representation of a crossing strategy enabling to obtain crops with improved value.

Figure 14:
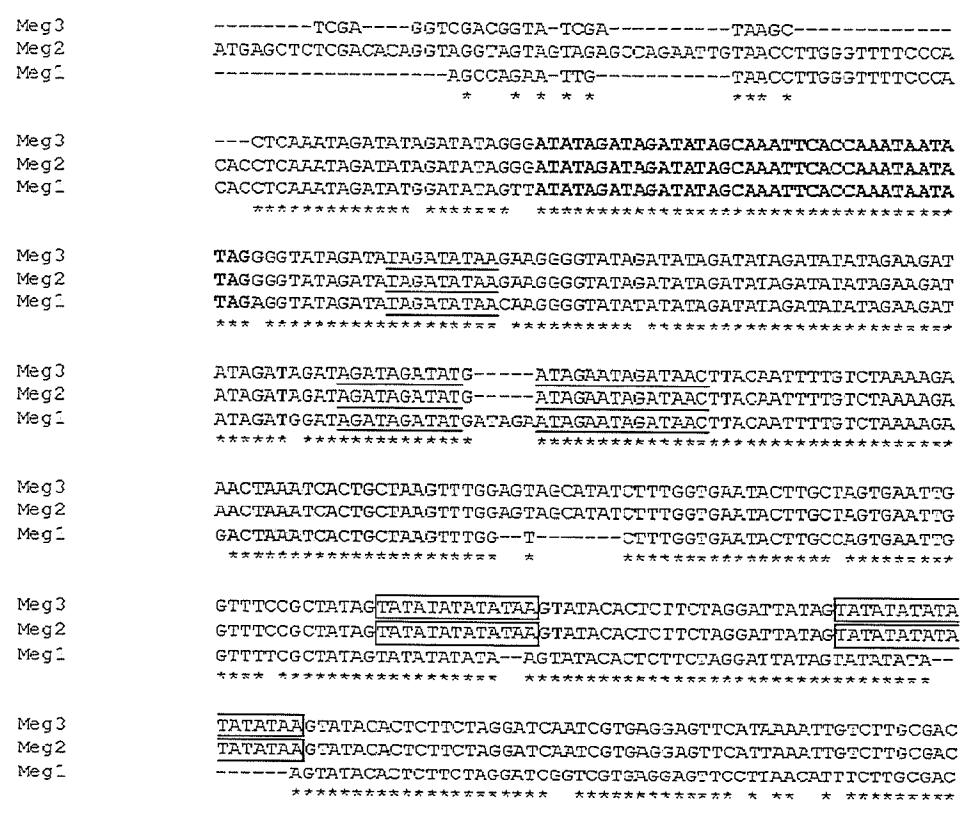

FIG. 14 depicts a pairwise sequence alignment of MEG1 (SEQ ID No: 1=promoter MEG 1-1), MEG2 (SEQ ID No: 2=promoter MEG 1-2), and MEG3 (SEQ ID No: 3=promoter MEG 1-3) performed with CLUSTAL W (1.74). The nucleotides shown in bold correspond to SEQ ID No: 57. Underlined nucleotides correspond to conserved regions between BETL specific genes (meg1, betl's and DD1s), and shaded nucleotides correspond to conserved region between the above genes and ESRs. Boxed nucleotides correspond to TATA boxes.

EXAMPLES

The invention will now be described by the way of the following examples, which should not be construed as in any way limiting the scope of the invention.

Several oligonucleotides and primers could be used to amplify or isolate the sequences or sequence fragments according to the present invention. The oligonucleotides and primers described are not limiting. The man skilled in the art knows how to design an oligonucleotide, or a specific oligonucleotide, based on a sequence.

Example 1

Plant Material and Growth Conditions

Maize (*Zea mays* L.) diploid inbred lines W22, F2, B73 and Mo17, and tetraploid W23 (COOP Maize Stock Centre) were glasshouse grown under the following regime: 16 h day length (supplemented with metal halide lamps at 250 mmols, when required) at 22-28° C. during the day, and at 16-20° C. at night. Humidity levels were set at approximately 40-50% daytime and 60-70% at night. All lines were selfed and reciprocally crossed, and kernels were harvested at 6-24 days after pollination (DAP). Embryos and endosperms were isolated and pooled, then frozen in liquid nitrogen and stored at −80° C.

Example 2

Identification and Characterization of the ZmMeg1 Gene Family

A genomic screen designed to identify endosperm transcripts showing parent-of-origin patterns of expression was carried out by allelic message display (AMD) (Gutiérrez-Marcos et al., 2003).

Allelic Message Display (AMD):

Total endosperm RNA was extracted from selfed and reciprocally-crossed inbred lines and used for AMD-PCR according to the protocol of Hagiwara et al. (1997).

Reverse transcribed RNA was used as source material for PCR (HIEROGLYPH kit; Genomix-Beckman), labeling with [alpha 33P]-dATP. A combination of 240 primers was used to carry out PCR reactions and products were analyzed in a semi-automatic Genomix LR DNA sequencing system. Following exposure to film (Biomax MR, Kodak), candidate bands were excised from the gel and amplified using PCR.

Figure 1:
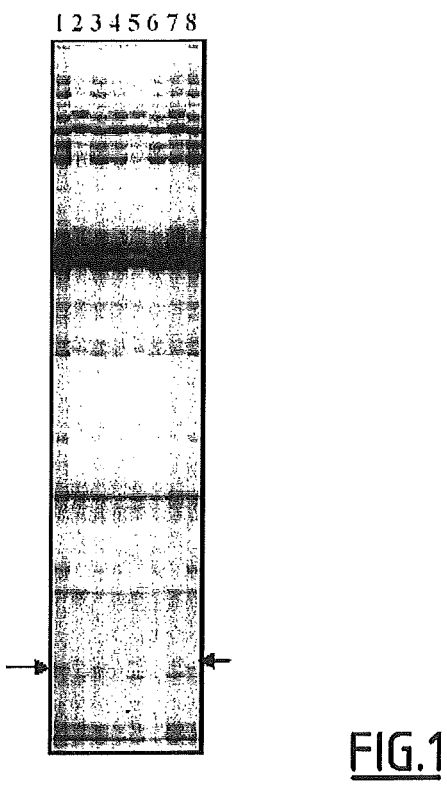
FIGS. 1 and 2 represent Allelic Message Display (AMD) analysis of ZmMEG1-1.

This resulted in the presence of several fragments showing monoallelic maternal expression, one of which was termed *Zea mays* maternally-expressed-gene1 (ZmMEG1) (FIG. 1).

Identification of ZmMEG1 cDNAs and Expression Analysis.

2.1) Isolation of Meg1 cDNA and Related Sequences:

Full length cDNAs were obtained after screening a 7 DAP maize endosperm cDNA library (Hueros et al., 1999b). Among the 500,000 plaques screened, five cDNA clones were identified and sequenced. This identified the full-length cDNA, ZmMEG1-1, plus three other similar, but not identical, cDNAs which we termed ZmMEG1-2, -3, and -4. After screening the maize genome database, a further two ESTs showing partial similarity to the C-terminus of the translated MEG1-1 protein sequence were identified and denominated ZmMEG1-5, and -6.

2.2) Mapping:

The ZmMEG1 gene family was mapped to the short arm of maize chromosome 7, between markers csu13 and bngl1200, by restriction fragment length polymorphism (RFLP) analysis using a population of immortalized F2 lines.

2.3) Southern Analysis:

The diversity of the ZmMEG1 family was revealed in the F2 inbred line by Southern analysis and BAC screening, this analysis indicated that the ZmMEG1 gene family comprises from two to four gene clusters with a few copies present in every cluster.

For Southern blotting, DNA was digested with the restriction enzyme XhoI, the hybridization solution was 5×SSPE/5×Denhardt's/0.5% SDS, and the blots were probed with full length Meg1-1 coding region (SEQ ID No: 5).

Southern analysis under high stringency conditions (hybridization 65° C. and wash for 10 minutes at 65° C. with 0.1×SSPE/0.5% SDS) revealed that the ZmMEG1 gene family comprises between 5-8 copies present in most maize inbred lines, teosintes and other grasses (rice, sorghum, sugar cane).

Southern analysis under low stringency conditions (hybridization 50° C. and wash for 10 minutes at 65° C. with 2×SSPE/0.5% SDS) also revealed bands in wheat and barley.

2.4) Expression Pattern:

The expression pattern of ZmMEG1-1 and the other ZmMEG1-like cDNAs (ZmMEG1-2, ZmMEG1-3, ZmMEG1-4, ZmMEG1-5, ZmMEG1-6) was assessed by reverse transcription-polymerase chain reaction (RT-PCR) using gene-specific oligonucleotide pairs shown in Table 1 below.

TABLE 1

List of oligonucleotides used for RT-PCR analysis.

| Gene Name | Forward Oligonucleotide | Reverse Oligonucleotide | PCR size (bp) |
|---|---|---|---|
| MEG1-1 | TGCTGCTCATGCGCATGGG GCTG, SEQ ID No: 23 | TTAGAAGCAKGCATG WCTACACTSAGCC, SEQ ID No: 24 | 165 |
| MEG1-2 | ATGCACATGGGAAGGGTCA TGTC, SEQ ID No: 25 | TTAGAAGCAKGCATG WCTACACTSAGCC, SEQ ID No: 26 | 193 |
| MEG1-3 | GCATAGCAGGAGTGGAGG GC, SEQ ID No: 27 | GAAGCAGGCATGACT ACACTC, SEQ ID No: 28 | 292 |
| MEG1-4 | TGGCCAATGTCGCCTCCG AG, SEQ ID No: 29 | TTAGAAGCAKGCATGW CTACACTSAGCC, SEQ ID No: 30 | 320 |
| MEG1-5 | ATGGCTGGCTATGGTGTT GATG, SEQ ID No: 31 | GTGCAGTTTGCAGGTA AGCCC, SEQ ID No: 32 | 150 |
| MEG1-6 | TGTACGCCTGACTTGGCT AGCAACC, SEQ ID No: 33 | TTAGAAGCAKGCATGW CTACACTSAGCC, SEQ ID No: 34 | 181 |
| GST | GCAACGTACCGTACCTTT CCGA, SEQ ID No: 35 | ACGCTGCATTCAATTA CCGGGAAG, SEQ ID No: 36 | |
| GUS | GGGCCAACAGTTCCTGAT TAACC, SEQ ID No: 55 | CCCCGTTGACTGCCTC TTCG, SEQ ID No: 56 | |

The expression pattern is shown in FIG. 4.

Specific ZmMeg1-1 alleles showed 99.9% identity in several inbred lines (A188, B73, Mo17, F2, W22 and tetraploid W23) and were detected using cleaved and amplified polymorphic sequences (Neff et al., 1998).

To distinguish between ZmMeg1-1 alleles, RT-PCR analysis was performed employing MEG1 (5'-TGCTGCTCAT-GCGCATGGGGCTG-3', SEQ ID No:17) and MEG1HpaI (5'-TTGTATATAAAAACAGTGATGTTAA-3', SEQ ID No: 18) primers to produced a DNA fragment that after HpaI digestion generated fragments of 177-bp for F2 and 198-bp for A69Y or W23.

The gluthatione synthase1 gene was used as a control for a biallelic parent-of-origin expression.

ZmMEG1-1 transcript was only present in endosperm samples between 4 and 20 DAP indicating that its expression is endosperm-specific. ZmMEG1-2 and ZmMEG1-4 also showed a similar pattern of expression, whereas ZmMEG1-3 was expressed in endosperm as well as in anther and pollen samples. By contrast, ZmMEG1-5 and ZmMEG1-6 were found to be expressed in most tissues tested.

Example 3

Parent-of-Origin Pattern of Expression of ZmMEG1-1

3.1) ZmMeg1-1 has a Maternal Parent-of-Origin Pattern of Expression

To confirm the maternal parent-of-origin expression pattern of ZmMEG1-1, a polymorphism was detected in the 3'UTR of the gene, between F2 and A69Y, and W23 and other inbred lines, which allowed us to design oligonucleotides for allele-specific RT-PCR.

The results revealed exclusive expression of the ZmMEG1-1 maternal allele at early stages of endosperm development (4 DAP) (FIG. 2). Surprisingly, it has been found that at later stages of endosperm development (12 DAP) ZmMEG1-1 expression became biallelic (FIG. 2).

To investigate the effects of altering the maternal to paternal genomic ratio in the endosperm on ZmMEG1-1 expression, reciprocal crosses between diploid and tetraploid inbred lines were performed. Allele-specific RT-PCR showed that the ZmMEG1-1 expression pattern remained unaltered (FIG. 2).

3.2) ZmMeg1-1 Alleles are Differentially Methylated in the Endosperm

Since ZmMEG1-1 is subjected to a parent-of-origin pattern of expression in the endosperm it can be predicted that changes in methylation might occur between the different parental alleles.

The inventors have tested this hypothesis by examining the methylation status of ZmMEG1-1 parental alleles using methylation-sensitive restriction enzyme digestion and Southern analysis with a gene specific probe on genomic DNA obtained from embryo and endosperm samples.

Differences in the methylation status of parental ZmMEG1-1 alleles were apparent in the endosperm alone; ZmMEG1-1 maternal alleles appeared demethylated whereas paternal alleles were methylated (FIG. 8).

These results strongly suggest a correlation between methylation status of a given ZmMEG1-1 allele in the endosperm and a parent-of-origin pattern of expression.

Example 4

ZmMeg1-1 Protein Characterisation 4.1) ZmMeg1-1 Encodes a Basal Endosperm Transfer Cell Wall Protein The full length ZmMEG1-1 cDNA contained an open reading frame of 88 amino acids (FIG. 3), encoding a predicted 9794 Da protein with a pI of 7.5. The ZmMEG1-1 polypeptide contains a hydrophobic N-terminal region with characteristics of a 27 amino acid signal peptide (von Heijne, 1986). Further analysis identified a putative cleavage site between His-26 and Glu-27, thus producing a polypeptide containing 61 amino acids, with a predicted molecular mass of 6730 Da and pI 6.2.

An interesting feature of the ZmMEG1 polypeptide is the presence of a highly conserved cysteine-rich domain in the C-terminal portion, also present in the ZmMEG1-likes (ZmMEG1-2, -3, -4, -5, and -6) (FIG. 3). This conserved region contains six cysteines and two tyrosines, and resembles other cysteine domains found in several plant proteins with hypothetical cell-wall localization (de Oliveira et al., 1990; Domingo et al., 1999).

In situ hybridization of ZmMEG1-1 was performed on kernel sections at various stages of endosperm development with a gene specific probe kernels according to a published method (Jackson, 1991), with minor modifications DB (Costa et al., 2003). (FIG. 5).

No signal was detected with the sense probe, however, the antisense probe only gave signal in the transfer cells from 4 DAP and showed maximum expression at around 6-10 DAP (FIG. 5), clearly indicating that ZmMEG1-1 is exclusively expressed in the basal transfer region of the endosperm.

4.2) ZmMEG1-1 Protein Localization:

To determine the localization of ZmMEG1-1 protein in maize endosperm, a polyclonal antiserum was raised by using a synthetic peptide designed to the N-terminus of the putatively processed ZmMEG1-1 polypeptide.

Immunolocalization

Polyclonal antiserum was raised in rabbit against a synthetic peptide (NAPAEEGILREKRAQC, SEQ ID No: 19) and affinity purified with an immobilized peptide using a Sulpholink coupling gel system (Pierce, UK). Maize kernels were fixed in 4% paraformaldehyde in 0.1 M sodium phosphate buffer pH 7.2, for 12-24 h depending on the tissue volume. Samples were dehydrated in an ethanol series and wax embedded. Sections were de-paraffinized and blocked in 1% BSA in PBS (10 mM sodium phosphate, 150 mM NaCl pH 7.4) for 30 min at room temperature, and incubated overnight with anti-MEG1 antiserum or pre-immune serum (both diluted 1:500). The immunoreactions was detected using alkaline phosphatase-coupled secondary antibody (Sigma; diluted 1:1000) and NBT/BCIP as substrate.

Immunolocalization was performed using the purified antiserum, which detected ZmMEG1-1 protein adjacent to the cell wall ingrowths of basal endosperm transfer cells (FIG. 6).

To obtain biochemical evidence of protein localization to the cell wall, protein extracts from 10 DAP endosperms were fractionated as described by Serna et al. (2001) and analyzed by immunoblotting (FIG. 7).

Subcellular Fractionation of Proteins

Fractionation of subcellular components of endosperms (F2 inbred) was performed as described by Serna et al. (2001). Proteins were fractionated by SDS-PAGE electrophoresis according to (Laemmli, 1970), and electroblotted onto a polyvinylidine difluoride (PVDF) membrane. Proteins were detected using an enhanced chemiluminescence method (ECL, Amersham, UK).

Several proteins with predicted molecular masses that ranged from 6 to 50 kDa were present in the cytoplasmic fractions, two of which corresponded to ca. 9-10 kDa and ca. 6-7 kDa. Interestingly, the ca. 6-7 kDa proteins gave the greatest signal intensity in the cell wall preparation, thus providing evidence for cell wall localization of the putative cleaved ZmMEG1-1 polypeptide (FIG. 7). Three other proteins with molecular masses between 2.5 to 3.5 kDa were observed in the cell wall fraction.

4.3) ZmMEG1-1 Role:

The BETL and BAP families comprise the largest basal transfer layer-specific protein families found to date. These small proteins are secreted into the pedicel region or are localized to the cell wall and are strongly suggested to be implicated in antifungal attack and pathogen defense (Hueros et al., 1995; Serna et al., 2001).

As known from the art (Hueros et al. 2002), the BETL-specific genes isolated to date share some structural features that strongly suggest that they play a role in defense against pathogen entry into the developing seed. They encode small, Cys-rich secreted peptides that accumulate only transiently during endosperm development.

Amino acid sequence analysis of ZmMeg1-1 revealed a cysteine-rich motif in the C-terminal region comprising six cysteine residues and two tyrosine residues: C-(X)4-CYCC-(X)8-Y-(X)4-C-(X)3-C (SEQ ID No: 20), which was conserved in the other ZmMEG1-like proteins (ZmMEG1-2, ZmMEG1-3, ZmMEG1-4, ZmMEG1-5 and ZmMEG1-6) (FIG. 3) and showed high similarity to many cysteine-rich domains identified in other plant proteins (Hueros et al., 1995; Domingo et al., 1999; Hueros et al., 1999b; Serna et al., 2001) (Schopfer et al., 1999). Cysteine-rich domains are believed to be required for the maintenance of particular protein conformations, which result in the exposure of inter-digitated side chain residues (Berg and Shi, 1996), such as tyrosine residues found in ZmMEG1. Importantly, it has been reported that exposure of tyrosine residues facilitate the binding of synthetic-proteins to the cell wall (reviewed in Cassab, 1998).

Since ZmMEG1-1 protein localization is proximal to the maternal-filial interface, it is strongly expected that it may have a defensin-like function, as reported for BETL1,3 (Hueros et al., 1995; Hueros at al., 1999a) and ZmES proteins (Cordts et al., 2001).

Furthermore the modification of MEG1 protein level modifies seed size as the decrease of MEG1 protein level induces a reduced seed size (see below).

An alignment of MEG1-1 and MEG1-2 amino acid sequence with that of BAPs proteins has been performed and the result is shown in FIG. 9.

Two Meg1 constructs (expression cassettes) to determine the effect of Meg1 gene overexpression in maize have been made:

Maize Transformation:

Embryogenic type II calli were transformed with the construct and regenerated as described by Bonello et al., 2000.

The following constructs have been obtained by classical molecular biology methods.

Construct A: p35S-HSP70intron-Meg1 genomic-3'CaMV 34 maize transformants have been generated, some plants exhibit improved resistance to the pathogens.

Construct B: p35S-HSP70intron-Meg1 cDNA-3'CaMV 36 maize transformants have been generated, some plants exhibit improved resistance to the pathogens.

Construct C: p35S Meg1-RNAi-3'OCS

A Meg1 construct (expression cassette) to determine the effect of Meg1 downregulation has been made.

Vector pGUSART, was obtained by subcloning an EcoRV fragment (789 to 1820) of the GUS gene into pART7 (Gleave A. P (1992) Plant Mol. Biol. 20:1203-1207).

A fragment of the Meg1-1 cDNA sequence (151 to 380) was amplified by PCR using two oligonucleotides:

```
meg1RNAi.FOR (ClaI-EcoRI)
                              (SEQ ID No: 63)
5'-ATCGATGAATTCGCTCAAGGGTTTCTTCCATG-3' meg1RNAi.REV (BamHI-XhoI)
                              (SEQ ID No: 64)
5'-GGATCCTCGAGCCTCTAGTATCGGTCTGAC-3'
```

The PCR product was subcloned into pGEM-T easy and sequenced. After digestion with BamHI and ClaI, and EcoRI and XhoI the fragments were subcloned into pGUSART to generate a 3'-5' and 5'-3' construct flanking the deleted portion of the GUS gene capable of produce a duplex formation.

24 maize transformants have been generated, some plants exhibit reduced resistance to the pathogens.

In particular, 4 out of the 24 Meg1 RNAi plants exhibited a segregation in seed size on the cob. Kernels that inherited the RNAi transgene were found to be smaller than wild type segregant kernels (figure not shown). Thus inhibition of Meg1 expression reduces seed size.

Example 5

ZmMEG1-1 Promoter Isolation and Sequence Characterization 5.1) Meg1 Genomic DNA Isolation A Meg1.1 probe was used to screen an F2 BAC library (O'Sullivan et al., 2001), resulting in six genomic ZmMeg1-1 fragments that were subcloned into pBluescript KSII (Stratagene, UK) and sequenced. Sequence analysis revealed the existence of at least four different copies of ZmMEG1-1 in the F2 inbred line, all of which showed subtle differences in their promoter region, yet highly conserved exon and intron regions. A minimal region of the promoter (ca. 370 bp) was found to be conserved across other promoters belonging to known basal endosperm transfer cell-specific genes (Hueros et al., 1999b; Sevilla-Lecoq et al., 2003) (FIG. 10).

5.2) Reporter Construct Preparation:

A minimal promoter region of ZmMEG1-1 was isolated by PCR using two specific oligonucleotides (5'-ACACCT-CAAATAGATATGGATATAG-3', SEQ ID No: 60, and 5'-GTCGCAAGAAATGTTAAGGAACTCC-3', SEQ ID No: 61) and subcloned into pGEM-T easy vector (Promega, Madison, USA).

After digestion with EcoRI and ClaI, the 371 bp fragment was fused to the β-glucoronidase (GUS) encoding sequence and the nopaline synthase (NOS) terminator of the pSLJ4K1 vector (Jones et al., 1992) to generate the transcriptional fusion vector denominated pZmMEG1-1-GUS.

5.3) Maize Transformation and Expression Analysis:

To test whether the minimal promoter region of ZmMEG1-1 was able to confer transfer cell-specific gene expression we stably transformed maize plants with the pZmMEG1-1-GUS transcriptional fusion construct.

Maize Transformation:

Embryogenic type II calli were transformed with the construct and regenerated as described by Bonello et al., 2000.

Five independent transgenic lines were generated (0757-1C, 0757-2E, 0757-2F, 0757-2D, 0757-2L) and selected on the basis of high levels of β-glucuronidase expression, as detected by histochemical staining of kernels. Plants were genotyped for β-glucuronidase (GUS) transcriptional fusions via PCR using GUS-specific oligonucleotides (SEQ ID No: 55 and 56). Histochemical analysis of transgeneic lines was performed according to (Jefferson et al., 1987; Costa et al., 2003). Briefly, fixed kernels were dehydrated to 70% ethanol before analysis and digitally imaged.

GUS staining was only ever observed in endosperm tissue, and not in any other plant tissues tested.

These lines were subsequently backcrossed with pollen from an A188 standard inbred for four consecutive generations to confirm the stable pattern of expression in the endosperm.

Two of the independent transgenic lines (0757-2E and 0757-2D) were randomly selected and reciprocally outcrossed with wild-type A188 plants to test for changes in patterns of transgene expression based on their parental mode of inheritance.

For each line, around 200-280 kernels at different developmental stages were isolated from four plants and histochemically stained for GUS. For each time point analyzed, around 50-70 kernels were isolated from four plants, and histochemically stained for GUS, as mentioned above.

Interestingly, we found differential temporal GUS expression when transmitted either maternally or paternally.

When pZmMEG1-1-GUS plants were either selfed or outcrossed as females, GUS staining was present in transfer cells from 4 DAP, when the endosperm becomes fully cellular, and remaining until 20 DAP. A maximum level of GUS staining was attained at 10-12 DAP.

However, when pZmMEG1-1-GUS plants were outcrossed as males (i.e. transmitted paternally through pollen), histochemical GUS activity was only ever detected after 10 DAP, when it was at its highest, and the declined in expression by 20 DAP. The apparent delay in expression of the paternally inherited transgene was confirmed at the transcriptional level by Northern analysis (data not shown).

Taken together, the data demonstrate that a minimal region of MEG1-1 promoter is able to confer different temporal transfer cell-specific expression of uidA reporter gene depending on parental origin.

So, expression of pZmMEG1:GUS in BETL cells is dependent on parental inheritance.

Example 6

Transactivation of the ZmMEG1-1 Promoter by ZmMRP1

It has been recently found that a transfer cell-specific transcription factor, ZmMRP1, is able to transactivate expression of several BETL promoters (Gomez et al., 2002).

To investigate whether ZmMRP1 was also capable of transactivating ZmMEG1-1, etiolated maize leaves were cobombarded with the pZmMEG1-1-GUS construct and a 35S enhanced version of the ZmMRP1 protein (p35S-MRP1 translational fusion).

The data showed that pZmMEG1-GUS was significantly transactivated by ZmMRP1 (FIG. 11), indicating that ZmMRP1 is sufficient for activation of ZmMEG1-1 in leaf tissues and is probably sufficient to activate ZmMEG1-1 expression in endosperm transfer cells.

The same results are obtained with the MEG1 promoter according to SEQ ID No: 62.

Example 7

Promoter Deletion Analysis

To define the region essential for transactivation by ZmMRP1, we generated a deletion series of the conserved ZmMEG1-1 promoter region and fused these to the uidA reporter gene.

The serial deletion analysis was performed by PCR amplification of different regions of the ZmMEG1-1 promoter, using multiple oligonucleotide pairs (see table 2 below) and then subcloning into pGEM-T easy vector (Promega, Madison, USA).

TABLE 2

List of oligonucleotides used in deletion analysis.

| Construct name | Forward Oligonucleotide | Reverse Oligonucleotide |
|---|---|---|
| pMEG1-GUS | ACACCTCAAATAGATATG GATATA, SEQ ID No: 37 | GTTATCTATTCTATTCTATC ATATCTATC, SEQ ID No: 38 |
| pMEG1-31/30GUS | GATATAGATATATAGAAG AGATATAGATGG, SEQ ID No: 39 | GTTATCTATTCTATTCTATC ATATCTATC, SEQ ID No: 40 |
| pMEG1-32/30GUS | AGATAGATATGATAGAAT AGATAGATAAC, SEQ ID No: 41 | GTTATCTATTCTATTCTATC ATATCTATC, SEQ ID No: 42 |
| pMEG1-33/30GUS | ATTTTGICTAAAGAGACT AAATCACTGC, SEQ ID No: 43 | GTTATCTATTCTATTCTATC ATATCTATC, SEQ ID No: 44 |
| pMEG1-30/31GUS | ACACCTCAAATAGATATG GATATA, SEQ ID No: 45 | CCAATTCACTGGGTTATCTA TTCTATTCTATCATATCT, SEQ ID No: 46 |
| pMEG1-30/32GUS | ACACCTCAAATAGATATG GATATA, SEQ ID No: 47 | CCAATTCACTGGCCATCTAT ATCTTCTATATATCTATA, SEQ ID No: 48 |
| pMEG1-30/33GUS | ACACCTCAAATAGATATG GATATA, SEQ ID No: 49 | CCAATTCACTGGCCCCTTGT TATATCTATATCTATACC, SEQ ID No: 50 |

Constructs were digested with EcoRI and BstXI and fragments were subcloned into the pZmMEG1-1-GUS construct pre-digested with EcoRI and BstXI. By following this approach the putative TATA boxes identified in the ZmMEG1-1 promoter remained intact.

The ZmMRP-1 coding region was isolated by PCR using oligonucleotides MRP.FOR (5'GGATCCATGAATC-CCAACTTCAACAGTG3', SEQ ID No:21) and MRP.REV (5'GAATTCTTATCGGTTATATATCTGGCTCTCC3', SEQ ID No:22). PCR fragments were subcloned in pGEM-T easy (Promega, Madison, USA), digested with BamHI/EcoRI and the 327 bp fragment was subcloned into the plasmid described by Pang et al. (1996) to generate p35S:HSP70::MRP1. Plasmid DNA was isolated by the QIAprep midi kit (Qiagen, Germany) and coated onto tungsten (M10) particles according to (Klein et al., 1992).

For transient transformation, Hi-II maize seeds were surface sterilized and germinated in the dark. Etiolated leaves (2 cm wide) were sectioned into 1-2 cm long pieces and cobombarded with ZmMEG1-1 promoter deletion and ZmMRP1 constructs using a BioRad Biolistic PDS-1000/He device. Gold particles (0.6 nm, from BioRad, UK) were coated with the DNA plasmid mixture including 2.5 g of p35S:MRP1 derived plasmid and 2.5 g of ZmMEG1-1 promoter deletion. Tissues were positioned 6 cm from the microcarrier stopping screen itself located 5 cm below the 6.2 Mpa rupture disc.

After bombardment, samples were incubated for 24 h at 26° C. in the dark on solid medium (Murashige and Skoog, 1962) containing 100 mg/l myoinositol, 2 g/l glutamine, 30 g/l sucrose, and Murashige and Skoog vitamins (Sigma, UK).

A minimum of three independent experiments were conducted for each promoter deletion made.

Histochemical detection of GUS expression was performed by staining the leaf discs according to (Jefferson, 1989) with modifications. Leaf pieces were stained in a medium containing 0.5 mg/ml Xglucuronide (Clonetech, Palo Alto, Calif.), 0.5 mM phosphate buffer, pH 7.0, 0.1% triton X-100 and 20% (v/v) methanol.

It has been found that removal of the distalmost portion of the promoter (−370 to −240 region) disabled transactivation of pZmMEG1 GUS by ZmMRP1.

To determine whether this minimal −370 to −250 promoter region (FIG. 12) was sufficient to allow transactivation by ZmMRP1, either alone or in combination with other regions within the conserved ZmMEG1-1 promoter, deletions were performed in the reverse orientation.

From this analysis, the −370 to −250 minimal promoter region in combination with the putative TATA box region (−127 to 1) was deemed sufficient to confer transactivation of the ZmMEG1-1 promoter by ZmMRP1.

Taken together, these results conclusively demonstrate that ZmMRP1 activates ZmMEG1-1 expression by transactivation of the −370 to −250 conserved domain also present in promoters of many BETL-specific genes.

The same results are obtained with the −345 to −251 region (95 nucleotides in length) that corresponds to nucleotides +26 to +120 of SEQ ID No:4 and with the fragment from nucleotide +29 to +119 of SEQ ID No:4 (91 nucleotides in length).

Example 8

Expression in the BETL Area of Genes of Interest

SEQ ID No: 1 and SEQ ID No: 62 have 90% identity and 6.7% of gaps after alignment on the basis of SEQ ID No: 1. This differences correspond to deletions, insertions, and base replacements that do not affect the functionality of the sequence so that same results are obtained with SEQ ID No: 1 and SEQ ID No: 62.

A MEG1 promoter according to the invention is useful to express from an early stage of BETL development proteins or RNA that result in desirable changes in seed development or quality. Such proteins or RNA may for example increase the size of the BETL layer and/or increase its capacity to import nutrients into the developing seed. Alternatively such proteins or RNA may improve resistance to pathogens and thus better protect the developing seed from transfer of pathogens from maternal tissues resulting in seeds (and progeny plants) of higher quality and vigour.

As an example of the first utility Meg1 promoter (Zm-MEG1-1) is linked to the cell wall invertase incW2 and as an example of the second utility Meg1 promoter (ZmMEG1-1) is linked to the anti-fungal protein BAP2.

8.1) Overexpression of IncW2 in the BETL

IncW2 is naturally expressed in the BETL. Its importance in the determination of seed size was demonstrated via the analysis of IncW2 mutants which exhibit a miniature kernel phenotype (Cheng et al (1996) Plant Cell Jun; 8 (6):971-983)).

Meg1-1 promoter is fused to the coding region of IncW2 and cloned into a binary vector for agrobacterial mediated transformation of maize. Analysis of the transformed plants indicates that some plants overexpress IncW2 and this expression is earlier than normal in seed development. These plants possess seeds that are larger than segregant seeds that lack the transgene which have normal levels of IncW2.

The same results are obtained with a construct comprising the MEG1 promoter as defined in SEQ ID No: 62.

8.2) Overexpression of BAP2 in the BETL

BAP2 is naturally expressed in the BETL. Its importance in resistance of the developing seed to fungal attack was strongly suggested in studies where the isolated protein demonstrated significant anti-fungal activity in vitro (Serna et al (2001)).

Meg1-1 promoter is fused to the coding region of BAP2 and cloned into a binary vector for agrobacterial mediated transformation of maize. Analysis of the transformed plants indicates that some plants overexpress BAP2 and this expression is earlier than normal in seed development. These plants possess seeds that have improved resistance to pathogens compared to segregant seeds that lack the transgene which have normal levels of BAP2.

The same results are obtained with a construct comprising the MEG1 promoter as defined in SEQ ID No: 62.

Example 9

Use of Meg1 Promoter to Improve the Crop Value

The Meg1-1 promoter is active earlier in the BETL if inherited from the female than from the male. Early overexpression of proteins in the BETL layer leading to a desirable kernel phenotype in some cases can disrupt the normal development of the kernel such that the germination of the kernel is reduced. For example early overexpression of the transactivator MRP1 (Gomez et al (2002)) in the BETL leads to seeds with a hypertrophied BETL layer. Since the BETL layer is important for nutrient flow into the developing endosperm, this hypertropy leads to the production of a larger endosperm and a larger seed. However in some genetic backgrounds or crops this hypertrophy gives a larger endosperm at the expense of embryo development. Thus although the resulting seed has a higher endosperm to embryo ratio and thus a higher value, the MPRP1 transgene is not utilisable due to poor seed germination.

Overexpression from an imprinted promoter, particularly such as ZmMEG1-1, overcomes this problem.

Maize plants were transformed with a construct comprising in the sens orientation the MEG1 promoter (as defined in SEQ ID No: 62), the ZmMRP1 cDNA, and the AtSac66 terminator (Jenkins et al. 1999).

Homozygous pMEG1:MRP1 plants are used as pollen donors in crosses to wild-type plants (poor germination of these plants is acceptable at the multiplication stage). All the hybrid progeny of this cross will have normal kernels since the late paternal expression of MRP1 has little effect on BETL size. The hybrid progeny of this cross will have 50% of kernels with increased endosperm size, enough to significantly improve the crop value (FIG. 13).

The same results are obtained with a construct comprising the MEG1 promoter as defined in SEQ ID No: 1 (pMEG1-1).

REFERENCES

An et al. (1986), Plant Physiology, 81:86-91
Anderson O. D. et al. (1989), Theor Appl Genet, 77:689-700
Allison et al. (1986); the MDMV leader (Maize Dwarf Mozaic Virus), Virology, 154:9-20
Berg, J. B., and Shi, Y. (1996). The galvanization of biology: a growing appreciation for the roles of zinc. Science 271, 1081-1085.
Bevan et al. (1983), Nature, 304:184-187
Bolchi, A., Petrucco, S., Tenca, P. L., Foroni, C. and Ottonello, S. (1999) Coordinate modulation of maize sulfate permease and ATP sulfurylase mRNAs in response to variations in sulfur nutritional status: stereospecific down-regulation by L-cysteine. Plant Mol. Biol. 39 (3), 527-537.
Bonello, J. F., Opsahl-Ferstad, H. G., Perez, P., Dumas, C., and Rogowsky, P. M. (2000). Esr genes show different levels of expression in the same region of maize endosperm. Gene 246, 219-227.
Callis et al. (1987), Genes Dev., 1:1183
Cassab, G I, Annual Review Of Plant Physiology And Plant Molecular Biology, 49: 281-309 1998
Cheng W. H., Taliercio E. W. and Chourey P. S. (1996). The Miniature1 Seed Locus of Maize Encodes a Cell Wall Invertase Required for Normal Development of Endosperm and Maternal Cells in the Pedicel. Plant Cell., 8 (6):971-983.
Christensen et al. (1996), Transgenic. Res., 5:213
Chupeau, M C et al 1989. Biotechnology vol. 7: pp. 503-508
Cordts, S., Bantin, J., Wittich, P. E., Kranz, E., Lorz, H., and Dresselhaus, T. (2001). ZmES gene encode peptides with structural homology to defensins and are specifically expressed in the female gametophyte. Plant Journal 25, 103-114.
Costa, L. M., Gutiérrez-Marcos, J. F., Greenland, A. J., Brutnell, T. P., and Dickinson, H. G. (2003). The globby1 (glo1-1) mutation disrupts nuclear and cell division in the developing maize seed causing aberrations in endosperm cell fate and tissue differentiation. Development (in press).
Dekeyser et al. (1988), Plant Physiology, 90:217-223
Della-Cioppa et al. (1987), Plant Physiology, 84:965-968
de Oliveira, D. E., Seurinck, J., Inze, D., Van Montagu, M., and Botterman, J. (1990). Differential expression of five Arabidopsis genes encoding glycine-rich proteins. Plant Cell 2, 427-436.
Depicker et al. (1992), Mol. Gen. Genet., 235 (2-3):389-396
Depigny-This et al. (1992), Plant Molecular Biology, 20:467-479

Domingo, C., Sauri, A., Mansilla, E., Conejero, V., and Vera, P. (1999). Identification of a novel peptide motif that mediates cross-linking of proteins to cell walls. Plant J 20, 563-570.

Eichholtz et al. (1987), Somatic Cell and Molecular Genetics, 13:67-76

Elroy-Stein, O., Fuerest, T. R., and Moss B. (1989), PNAS USA, 86:6126-6130

Finer J. (1992) Plant Cell Report 11:323-328.

Franck et al. (1980), Cell, 21 (1):285-94

Gallie, D. R. et al. (1989), Molecular Biology of RNA, pages 237-256

Gleave A. P (1992). Plant Mol. Biol. 20:1203-1207

Gomez et al. (2002), "Establishment of Cereal Endosperm Expression Domains: Identification and properties of a Maize transfer cell-specific transcriptional factor, ZmMRP-1". Plant Cell, 14, 599-610

Gritz et al. (1983), Gene, 25:179-188

Guerche et al. (1987), Mol. Gen. Genet., 206:382

Gutiérrez-Marcos, J. F., Pennington, P. D., Costa, L. M., and Dickinson, H. G. (2003). Imprinting in the endosperm: a possible role in preventing wide hybridization. Phil. Trans. R. Soc. London B. (in press).

Hagiwara, Y., Hirai, M., Nishiyama, K., Kanazawa, I., Ueda, T., Sakaki, Y., and Ito, T. (1997). Screening for imprinted genes by allelic message display: identification of a paternally expressed gene impact on mouse chromosome 18. Proc Natl Acad Sci USA 94, 9249-9254.

Hauptmann et al. (1988), Plant Physiology, 86:602-606

Hueros, G., Varotto, S., Salamini, F., and Thompson, R. D. (1995). Molecular characterization of BET1, a gene expressed in the endosperm transfer cells of maize. Plant Cell 7, 747-757.

Hueros, G., Royo, J., Maitz, M., Salamini, F., and Thompson, R. D. (1999a). Evidence for factors regulating transfer cell-specific expression in maize endosperm. Plant Mol Biol 41, 403-414.

Hueros, G., Gomez, E, Cheikh, N., Edwards, J., Weldon, M., Salamini, F., and

Thompson, R. D. (1999b). Identification of a promoter sequence from the BETL1 gene cluster able to confer transfer-cell-specific expression in transgenic maize. Plant Physiol 121, 1143-1152.

Ishida et al., (1996), Nature biotechnology, 14, 745-750

Jackson, D. (1991). In situ hybridisation in plants. In Molecular plant biology: a practical approach, D. J. Bowles, S. J. Gurr, and M. McPherson, eds (Oxford: Oxford University Press), pp. 163-174.

Jang et al., (1997) Plant Cell, 9, 5-19

Jefferson, R. A., Kavanagh, T. A., and Bevan, M. W. (1987). GUS fusions: betaglucuronidase as a sensitive and versatile gene fusion marker in higher plants. EMBO J 6, 3901-3907.

Jefferson, R. A. (1989). The GUS reporter gene system. Nature 342, 837-838.

Jenkins et al., (1999). Dehiscence-related expression of an Arabidopsis thaliana gene encoding a polygalactoronase in transgenic plants of Brassica napus. Plant Cell and Environment 22,159-167.

Jobling, S. A., and Gehrke, L. (1987), Nature, 325:622-625

Jones, J. D., Shlumukov, L., Carland, F., English, J., Scofield, S. R., Bishop, G. J., and Harrison, K. (1992). Effective vectors for transformation, expression of heterologous genes, and assaying transposon excision in transgenic plants. Transgenic Res 1, 285-297.

Jouanin et al. (1987), Plant Science, 53:53-63

Kay et al. (1987), Science, 236:1299-1302

Laemmli, U. K. (1970). Cleavage of structural proteins during the assembly of the head of bacteriophage T4. Nature 227, 680-685.

Lobreaux S. Massenet O. and J. F. Briat (1992). Iron induces ferritin synthesis in maize plantlets. Plant Molecular Biology 19: 563-575.

Lommel, S. A. et al. (1991), Virology, 81:382-385

Maas et al. (1991), Plant Molecular Biology, 16:199

Macejack, D. G., and P. Sarnow (1991), Nature, 353:90-94

Mary E Knight et al. (1998), Molecular cloning of starch synthase I from maize (W64) endosperm and expression in Escherichia coli. The Plant Journal 14 (5), 613-622.

McElroy et al. (1990), Plant Cell, 2:163-171

Meijer et al. (1991), Plant Molecular Biology, 16:807-820

Ming Gao et al. (1997), Independent genetic control of maize starch-branching enzymes IIa and IIb, Plant Physiol 114: 69-78.

Morris et al. (1992), Virology, 187:633

Mullis, K B (1987), Methods in Enzymology 155:335

Murashige, T., and Skoog, F. (1962). A revised medium for rapid growth and bio assays with tobacco tissue cultures. Physiol. Plant 15, 473.

Neff, M. M., Neff, J. D., Chory, J., and Pepper, A. E. (1998). dCAPS, a simple technique for the genetic analysis of single nucleotide polymorphisms: experimental applications in Arabidopsis thaliana genetics. Plant J 14, 387-392.

Ohta et al. (1990), Plant Cell Physiology, 31:805

O'Sullivan, D. M., Ripoll, P. J., Rodgers, M., and Edwards, K. J. (2001). A maize bacterial artificial chromosome (BAC) library from the European flint inbred line F2. TAG 103, 425-432.

Pang, S. Z., DeBoer, D. L., Wan, Y., Ye, G., Layton, J. G., Neher, M. K., Armstrong, C. L., Fry, J. E., Hinchee, M. A., and Fromm, M. E. (1996). An improved green fluorescent protein gene as a vital marker in plants. Plant Physiol 112, 893-900.

Poole et al., (1985), Cell, 40:37-43

Roberts et al. (1989), Plant cell, 1:569-578

Rogowsky, P. M. (2003). Analysis of ZmAE3 upstream sequences in maize endosperm and androgenic embryos. Sex. Plant Reprod. 16, 1-8.

Sambrook et al. (1989), Molecular Cloning, A Laboratory Manual, Cold Spring Harbour Laboratory Press p. 9.54-9.62

Serna et al. (2001) Maize endosperm secretes a novel antifungal protein into adjacent maternal tissue Plant Journal 25,687-698.

Sevilla-Lecoq, S., Deguerry, F., Matthysrochon, E., Perez, P., Dumas, C., and

Snowdon et al. (1996), Plant Molecular Biology, 31:689

Taliercio E W, Kim J-Y, Mahe A., Shanker S., Choi J., Cheng W-H, Prioul J-L and P. S. Chourey, (1999). Isolation, Characterization and Expression Analyses of two Cell Wall Invertase in maize. J. Plant Physiol. Vol. 155 pp. 197-204.

Thomas W. Greene and L. Curtis Hannah (1998), Maize endosperm ADP-Glucose Pyrophosphorylase SHRUNKEN2 and BRITTLE2 subunit interactions. The Plant Cell, Vol. 1295-1306.

Vancanneyt et al. (1990), Molecular and General Genetics, 220:245-250 von Heijne, G. (1986). A new method for predicting signal sequence cleavage site. Nucleic Acids Res 14, 4683-4690.

Watson et al. (1994) Ed. De Boeck Université, pp 273-292.

White, J., Chang S-YP., Bibb, M J. and Bibb, M J. (1990) Nucl. Acid. Res. 18, 1062.

Yoder et al., (1993) Biotechnology, 12, 263-292.

Zhang et al. (1995). Isolation and Characterization of an ipt gene from the Ti plasmid Bo542. Planta, 196:84-94.

The invention claimed is:

1. An expression cassette comprising an isolated nucleic acid molecule that has promoter activity specific to the endosperm and that comprises a DNA sequence selected from the group consisting of:

a. the sequence of SEQ ID NO: 62; and b. a fragment of the sequence as defined in (a), wherein said sequence has promoter activity specific to the endosperm operatively linked to at least one gene of interest of heterologous origin.

2. The expression cassette according to claim 1, wherein said gene of interest is selected from the group consisting of a sequence that encodes a peptide or a protein, an antisense RNA sequence, a sense RNA sequence and a ribozyme.

3. The expression cassette according to claim 1, in which the gene of interest encodes a protein selected from the group consisting of a protein involved in development of the embryo and/or of the endosperm, in determination of seed size and/or quality, in cell growth, or in sugar or fatty acid metabolism, in nutrient transfer, of a toxic protein, a transcription inhibiting protein, and a protein improving resistance to pathogens.

4. The expression cassette according to claim 1, which further comprises a selection marker gene for plants.

5. The expression cassette according to claim 1, which further comprises a gene encoding a MRP 1 protein.

6. An expression vector containing at least an expression cassette according to claim 1.

7. A host cell containing at least a vector according to claim 6.

8. A transgenic plant, or a part of a transgenic plant comprising a cell according to claim 7.

9. The plant or part of a plant according to claim 8, wherein said plant or part of plant is a cereal or oily plant.

10. The plant or part of a plant according to claim 9, which is from the group consisting of maize, rice, wheat, barley, rape, and sunflower.

11. A hybrid transgenic plant obtained by a cross of a plant comprising the expression cassette of claim 1.

12. A method of obtaining a plant having improved agronomic qualities and/or improved resistance to a pathogen, comprising the steps consisting of:
   a. transforming at least one plant cell by means of at least a vector according to claim 6;
   b. cultivating the cell(s) thus transformed so as to generate a plant containing in its genome at least an expression cassette according to claim 1, whereby a plant having improved agronomic qualities and/or improved resistance to a pathogen is obtained.

\* \* \* \* \*

SEQUENCE LISTING

<160> NUMBER OF SEQ ID NOS: 70

<210> SEQ ID NO 1
<211> LENGTH: 370
<212> TYPE: DNA
<213> ORGANISM: Zea mays
<220> FEATURE:
<221> NAME/KEY: misc_feature
<223> OTHER INFORMATION: promoter Meg1-1

<400> SEQUENCE: 1

```
agccagaatt gtaaccttgg gttttcccac acctcaaata gatatggata tagttatata      60
gatagatata gcaaattcac caaataatat agaggtatag atatagatat aacaaggggt     120
atatatatag atatagatat atagaagata tagatggata gatagatatg atagaataga    180
atagataact tacaattttg tctaaaagag actaaatcac tgctaagttt ggtctttggt    240
gaatacttgc cagtgaattg gttttcgcta tagtatatat ataagtatac actcttctag    300
gattatagta tatataagta tacactcttc taggatcggt cgtgaggagt tccttaacat    360
ttcttgcgac                                                            370
```

<210> SEQ ID NO 2
<211> LENGTH: 415
<212> TYPE: DNA
<213> ORGANISM: Zea mays
<220> FEATURE:
<221> NAME/KEY: misc_feature
<223> OTHER INFORMATION: promoter Meg1-2

<400> SEQUENCE: 2

```
atgagctctc gacacaggta ggtagtagta gagccagaat tgtaaccttg gttttccca      60
cacctcaaat agatatagat atagggtata gatagatat agcaaattca ccaaataata    120
taggggtata gatatagata taagaagggg tatagatata gatatagata tatagaagat    180
atagatagat agatagatat gatagaatag ataacttaca attttgtcta aaagaaacta    240
aatcactgct aagtttggag tagcatatct ttggtgaata cttgctagtg aattggtttc    300
cgctatagta tatatatata agtatacact cttctaggat tatagtatat atatatatat    360
aagtatacac tcttctagga tcaatcgtga ggagttcatt aaattgtctt gcgac         415
```

<210> SEQ ID NO 3
<211> LENGTH: 376
<212> TYPE: DNA
<213> ORGANISM: Zea mays
<220> FEATURE:
<221> NAME/KEY: misc_feature
<223> OTHER INFORMATION: promoter Meg1-3

<400> SEQUENCE: 3

```
tcgaggtcga cggtatcgat aagcctcaaa tagatataga tagggata tagatagata      60
tagcaaattc accaaataat ataggggtat agatatagat ataagaaggg gtatagatat    120
agatatagat atatagaaga tatagataga tagatagata tgatagaata gataacttac    180
aattttgtct aaaagaaact aaatcactgc taagtttgga gtagcatatc tttggtgaat    240
acttgctagt gaattggttt ccgctatagt atatatatat aagtatacac tcttctagga    300
ttatagtata tatatatata taagtataca ctcttctagg atcaatcgtg aggagttcat    360
aaaattgtct tgcgac                                                    376
```

```
<210> SEQ ID NO 4
<211> LENGTH: 121
<212> TYPE: DNA
<213> ORGANISM: Zea mays
<220> FEATURE:
<221> NAME/KEY: misc_feature
<223> OTHER INFORMATION: nucleotides 1 to 121 of promoter Meg1-1

<400> SEQUENCE: 4
agccagaatt gtaaccttgg gttttcccac acctcaaata gatatggata tagttatata      60
gatagatata gcaaattcac caaataatat agaggtatag atatagatat aacaaggggt     120
a                                                                    121

<210> SEQ ID NO 5
<211> LENGTH: 414
<212> TYPE: DNA
<213> ORGANISM: Zea mays
<220> FEATURE:
<221> NAME/KEY: misc_feature
<223> OTHER INFORMATION: MEG1-1 cDNA

<400> SEQUENCE: 5
cgtgaggagt tccttaacat ttcttgcgac atggagtaca aaagagggt ggatgcgcta       60 gtgttttctct ctttacttct cctaggatac tttgctgctc atgcgcatgg ggctgaagaa    120
ggaattttgc gagaaaaaag agcacaatgc gctcaagggt ttcttccatg caagataac     180 aagtgctact gttgcattgg gggccgaact catgattgct actatacgat ggctcagtgt    240
agtcatgcat gcttctaatc aaaaattaag atcactgttt ttatatacaa tgtaatggta    300
ggcaatgcta ttaataatac ataagggaat tttagttttg gtattagaat ttttctgatt    360
gacgaaattt agtcagaccg atactagagg cttaaaaaaa aaaaaaaaaa aaaa          414

<210> SEQ ID NO 6
<211> LENGTH: 75
<212> TYPE: PRT
<213> ORGANISM: Zea mays
<220> FEATURE:
<221> NAME/KEY: MISC_FEATURE
<223> OTHER INFORMATION: MEG1-1

<400> SEQUENCE: 6

Met Glu Tyr Lys Lys Arg Val Asp Ala Leu Val Phe Phe Ser Leu Leu
1               5                   10                  15

Leu Leu Gly Tyr Phe Ala Ala His Ala His Gly Ala Glu Glu Gly Ile
            20                  25                  30

Leu Arg Glu Lys Arg Ala Gln Cys Ala Gln Gly Phe Leu Pro Cys Lys
        35                  40                  45

Asp Asn Lys Cys Tyr Cys Cys Ile Gly Gly Arg Thr His Asp Cys Tyr
    50                  55                  60

Tyr Thr Met Ala Gln Cys Ser His Ala Cys Phe
65                  70                  75

<210> SEQ ID NO 7
<211> LENGTH: 383
<212> TYPE: DNA
<213> ORGANISM: Zea mays
<220> FEATURE:
<221> NAME/KEY: misc_feature
<223> OTHER INFORMATION: Meg1-2 cDNA

<400> SEQUENCE: 7
tcggcacgag gctacatgga gtacagaaag agggtggatg cgctagtgtt tttctcgtta     60
```

```
cttctcctcg gatactttgc tgctcatgca catgggaagg gtcatgtcac agatgatgtc     120
ggtgtttcta ctccagctaa agaaggaatt atgcaaggaa acggagcacg atgcgttgta     180
gggtttcctc catgcaaaga taacaagtgc tactgctgca ttgggggggcg aactcatgct    240 cgctactcta cgatggctga gtgtagacat gcctgcttct aaacacaaat taagatcgct    300
gttattatat acattgtaat ggtaggtaat gctattaata atatatggga attttagttt    360
tggtaaaaaa aaaaaaaaaa aaa                                            383

<210> SEQ ID NO 8
<211> LENGTH: 88
<212> TYPE: PRT
<213> ORGANISM: Zea mays
<220> FEATURE:
<221> NAME/KEY: MISC_FEATURE
<223> OTHER INFORMATION: MEG1-2

<400> SEQUENCE: 8

Met Glu Tyr Arg Lys Arg Val Asp Ala Leu Val Phe Phe Ser Leu Leu
 1               5                  10                  15

Leu Leu Gly Tyr Phe Ala Ala His Ala His Gly Lys Gly His Val Thr
            20                  25                  30

Asp Asp Val Gly Val Ser Thr Pro Ala Lys Glu Gly Ile Met Gln Gly
        35                  40                  45

Asn Gly Ala Arg Cys Val Val Gly Phe Pro Pro Cys Lys Asp Asn Lys
    50                  55                  60

Cys Tyr Cys Cys Ile Gly Gly Arg Thr His Ala Arg Tyr Ser Thr Met
65                  70                  75                  80

Ala Glu Cys Arg His Ala Cys Phe
                85

<210> SEQ ID NO 9
<211> LENGTH: 786
<212> TYPE: DNA
<213> ORGANISM: Zea mays
<220> FEATURE:
<221> NAME/KEY: misc_feature
<223> OTHER INFORMATION: MEG1-3 cDNA

<400> SEQUENCE: 9
ggcacgagga ggagttcctt aaattttctt gcgacatgga gtacagaaag agggtggatg     60
cgctagtgtt tttctcgtta ctcctcctca gatactttgc tgctcatgca catgggaagg    120
gtaagtgcta ctgctgcatt gggggcgatg tagggtttcc tccatgcaaa gataacaagt    180
gctactgctg cattggggggg cgaactcatg ctcgctactc tacgctggct gagtgtagtc    240
atgcctgctt ctaaacaaaa attaagatca ctgttattat acattgta atggtaggta     300 atgctattaa taatatatgg gaattttagt tttggtatta ctttttttc caattcacga    360 aataccttct aaaacctggc gtgacaggtg gcatagcagg agtggagggc agcgacggct    420
gcacagcgct gcatgcagtg gcttgcattt gtagctcctc gttggcgatg cgtgtgcgac    480
caagagctct cggcacagac aggtcatgtc acagatgatg tcggagtttc tactccagct    540
aaagaaggaa ttatgcaagg aaacggagca cgatgcgatg tagggtttcc tccatgcaaa    600
gataacaagt gctactgctg cattggggggg cgaactcatg ctcgctactc tacgctggct    660
gagtgtagtc atgcctgctt ctaaacaaaa attaagatca ctggtattat atacattgta    720
atgggtaggt aatgctatta ataatatatg ggaatttaag ttttggtatt aaaaaaaaaa    780
aaaaaa                                                               786
```

-continued

```
<210> SEQ ID NO 10
<211> LENGTH: 72
<212> TYPE: PRT
<213> ORGANISM: Zea mays
<220> FEATURE:
<221> NAME/KEY: MISC_FEATURE
<223> OTHER INFORMATION: MEG1-3, first ORF

<400> SEQUENCE: 10

Met Glu Tyr Arg Lys Arg Val Asp Ala Leu Val Phe Phe Ser Leu Leu
1               5                   10                  15

Leu Leu Arg Tyr Phe Ala Ala His Ala His Gly Lys Gly Lys Cys Tyr
            20                  25                  30

Cys Cys Ile Gly Gly Asp Val Gly Phe Pro Pro Cys Lys Asp Asn Lys
        35                  40                  45

Cys Tyr Cys Cys Ile Gly Gly Arg Thr His Ala Arg Tyr Ser Thr Leu
    50                  55                  60

Ala Glu Cys Ser His Ala Cys Phe
65                  70

<210> SEQ ID NO 11
<211> LENGTH: 667
<212> TYPE: DNA
<213> ORGANISM: Zea mays
<220> FEATURE:
<221> NAME/KEY: misc_feature
<223> OTHER INFORMATION: MEG1-4 cDNA

<400> SEQUENCE: 11
aagaccacca cccttgccga atccggcacc catgccatgc ccacttccac cgccaaggcc      60
atcgccgccg ccaagaccac caccettgcc gaatccggca cccatgccat gtccacttcc    120
accaccaagg cccccgccgc caccagcacc gtagccacta ccgccgccaa gaccaccacc    180
gcctttgccg aatccaccac ccatgccatg cccaattcca ccacctttgc catggcctcc    240
acccatgcca tggccaatgt cgcctccgag tccgccacct ttgccatatc caccaccaag    300
gccaccgcct tttcttaaat tgtcttgcga catggagtac agaaagaggg tggatgcgct    360
agtgtttttc tcgttacttc tcctcggata ctttgctgct catgcacatg gaaaggctaa    420
agaaggaatt atgcaaggaa acggagcacg atgcgttgtg gggtttcctc catgcaaaga    480
taacaagtgc tactgttgca ttgggggggcg aactcatgct cgctactcta cgatggctga    540
gtgtagtcat gcctgcttct aaacaaaaat taagatcgat gttattatat aaattgtaat    600
ggtaggtaat gctattaata atatatggga attttagttt tggtaattaa aaaaaaaaa    660 aaaaaaa                                                              667

<210> SEQ ID NO 12
<211> LENGTH: 76
<212> TYPE: PRT
<213> ORGANISM: Zea mays
<220> FEATURE:
<221> NAME/KEY: MISC_FEATURE
<223> OTHER INFORMATION: MEG1-4

<400> SEQUENCE: 12

Met Glu Tyr Arg Lys Arg Val Asp Ala Leu Val Phe Phe Ser Leu Leu
1               5                   10                  15

Leu Leu Gly Tyr Phe Ala Ala His Ala His Gly Lys Ala Lys Glu Gly
            20                  25                  30

Ile Met Gln Gly Asn Gly Ala Arg Cys Val Val Gly Phe Pro Pro Cys
        35                  40                  45
```

```
Lys Asp Asn Lys Cys Tyr Cys Cys Ile Gly Gly Arg Thr His Ala Arg
    50                  55                  60
Tyr Ser Thr Met Ala Glu Cys Ser His Ala Cys Phe
65                  70                  75

<210> SEQ ID NO 13
<211> LENGTH: 621
<212> TYPE: DNA
<213> ORGANISM: Zea mays
<220> FEATURE:
<221> NAME/KEY: misc_feature
<223> OTHER INFORMATION: MEG1-5 cDNA

<400> SEQUENCE: 13
tgcagggatg gctggctatg gtgttgatgg tcagcgtatg atgggtgttg ttggtatgga      60
cagcagaggg atgggatatg gtggcagacc tgagccacct cttccgcctg atgcatcaag     120
cactctatat attgagggct tacctgcaaa ctgcacacga cgggaggttt cacatatatt     180
tcgcccattt gttggttttc gtgaagttcg tcttgtcaac aaggagtcca gacatcctgg     240
tggagatcca catgtgttgt gtttcgtcga ttttgacaac cctgctcagg ctacaattgc     300
tctggaagca ttacaaggtc atgtcacgga tgatgtcaat gtttctgctc cagctgaaga     360
aggaattttg cgagaaaaaa gagcacaatg cgctcaaggg tttcttccat gcaaagataa     420
caagtgctac tgttgcattg ggggccgaac tcatgattgc tactatacga tggctcagtg     480
tagtcatgca tgcttctaat caaaaattaa gatcactgtt tttatataca atgtaatggt     540
aggcaatgct attaataata cataagggaa ttttattttg gtattagaat ttttctgatt     600
gacgaaaaaa aaaaaaaaaa a                                               621

<210> SEQ ID NO 14
<211> LENGTH: 142
<212> TYPE: PRT
<213> ORGANISM: Zea mays
<220> FEATURE:
<221> NAME/KEY: MISC_FEATURE
<223> OTHER INFORMATION: MEG1-5

<400> SEQUENCE: 14

Met Gly Tyr Gly Gly Arg Pro Glu Pro Pro Leu Pro Pro Asp Ala Ser
1               5                   10                  15

Ser Thr Leu Tyr Ile Glu Gly Leu Pro Ala Asn Cys Thr Arg Arg Glu
            20                  25                  30

Val Ser His Ile Phe Arg Pro Val Gly Phe Arg Glu Val Arg Leu
        35                  40                  45

Val Asn Lys Glu Ser Arg His Pro Gly Gly Asp Pro His Val Leu Cys
    50                  55                  60

Phe Val Asp Phe Asp Asn Pro Ala Gln Ala Thr Ile Ala Leu Glu Ala
65                  70                  75                  80

Leu Gln Gly His Val Thr Asp Asp Val Asn Val Ser Ala Pro Ala Glu
                85                  90                  95

Glu Gly Ile Leu Arg Glu Lys Arg Ala Gln Cys Ala Gln Gly Phe Leu
            100                 105                 110

Pro Cys Lys Asp Asn Lys Cys Tyr Cys Ile Gly Gly Arg Thr His
        115                 120                 125

Asp Cys Tyr Tyr Thr Met Ala Gln Cys Ser His Ala Cys Phe
    130                 135                 140

<210> SEQ ID NO 15
```

```
<211> LENGTH: 974
<212> TYPE: DNA
<213> ORGANISM: Zea mays
<220> FEATURE:
<221> NAME/KEY: misc_feature
<223> OTHER INFORMATION: MEG1-6 cDNA

<400> SEQUENCE: 15
tgcggaccca tgtcgttgtg caacgcgtgc gggatccgta ccggaagaag agacgggagc    60
catgggcctc gagtccagca gcaaggccgc caccgccggc ggcagcgagc accagcagca   120
gcagcggaag aagaaggcca cccgcgcgcg cggccgcttc ctccaagcgg agagggaga    180 gggagcggga gcgggagcgg aacaaggagg cggacgaggt caccgtggag ctccgcgcgg   240
tggggttcgg caaggaggtg gtgctgaagc agcggcggcg gatgcggcgg aggcgccgcc   300
tgggcgagga ggagcgcgcg gccatcctgc tcatggcgct ctcctccggc gtcgtgtacg   360
cctgacttgg ctagcaaccg cgccggcccc cgagacgccg cgcccaaagg cggcgaaagg   420
agaggagggc ccgattcgct ggacgtgcgg catgatctga gccccagaca gatccgtccg   480
tctggatcta tgctaagttt cccggctaa gtagtagctc gtcggttcga acaaggcgag    540
ttaataatcc gtgtccgcgc taggctagca gctctgttcc tctctccccc tcccgttgct   600
tgctgtgttc ttgccaccgc ctcctctagt tgtaatcctg ccgctagtag tgtgctagta   660
gtagctgtcc tgctgtaacc ttctcttgca atgtaaggag agattatatg gttaaaaaca   720
cagatgatgt cagtgtttct actccagcta agaaggaat tatgcaagga aacggagcat    780
ggtgcgttgt agggtttcct ccatgcaaag ataacaagtg ctactgctgc attgggggc     840 gaactcatgc tcgctactct acgatggctg agtgtagaca tgcctgcttc taaacaaaaa   900
ttaagatcgc tgttattata tacattgtaa tggtaggtaa tgctattaat aatatatggg   960
aattttagtt ttgg                                                    974

<210> SEQ ID NO 16
<211> LENGTH: 61
<212> TYPE: PRT
<213> ORGANISM: Zea mays
<220> FEATURE:
<221> NAME/KEY: MISC_FEATURE
<223> OTHER INFORMATION: MEG1-6

<400> SEQUENCE: 16

Met Val Lys Asn Thr Asp Asp Val Ser Val Ser Thr Pro Ala Lys Glu
1               5                   10                  15

Gly Ile Met Gln Gly Asn Gly Ala Trp Cys Val Val Gly Phe Pro Pro
            20                  25                  30

Cys Lys Asp Asn Lys Cys Tyr Cys Cys Ile Gly Gly Arg Thr His Ala
        35                  40                  45

Arg Tyr Ser Thr Met Ala Glu Cys Arg His Ala Cys Phe
    50                  55                  60

<210> SEQ ID NO 17
<211> LENGTH: 23
<212> TYPE: DNA
<213> ORGANISM: Artificial
<220> FEATURE:
<223> OTHER INFORMATION: oligonucleotide

<400> SEQUENCE: 17
tgctgctcat gcgcatgggg ctg                                           23

<210> SEQ ID NO 18
```

```
<211> LENGTH: 25
<212> TYPE: DNA
<213> ORGANISM: Artificial
<220> FEATURE:
<223> OTHER INFORMATION: oligonucleotide

<400> SEQUENCE: 18
ttgtatataa aaacagtgat gttaa                                          25

<210> SEQ ID NO 19
<211> LENGTH: 16
<212> TYPE: PRT
<213> ORGANISM: Artificial
<220> FEATURE:
<223> OTHER INFORMATION: Synthetic peptide

<400> SEQUENCE: 19

Asn Ala Pro Ala Glu Glu Gly Ile Leu Arg Glu Lys Arg Ala Gln Cys
1               5                   10                  15

<210> SEQ ID NO 20
<211> LENGTH: 27
<212> TYPE: PRT
<213> ORGANISM: Artificial
<220> FEATURE:
<223> OTHER INFORMATION: Cystein-rich peptide
<220> FEATURE:
<221> NAME/KEY: MISC_FEATURE
<222> LOCATION: (1)..(27)
<223> OTHER INFORMATION: Xaa = amino acid

<400> SEQUENCE: 20

Cys Xaa Xaa Xaa Xaa Cys Tyr Cys Cys Xaa Xaa Xaa Xaa Xaa Xaa
1               5                   10                  15

Xaa Tyr Xaa Xaa Xaa Xaa Cys Xaa Xaa Xaa Cys
            20                  25

<210> SEQ ID NO 21
<211> LENGTH: 28
<212> TYPE: DNA
<213> ORGANISM: Artificial
<220> FEATURE:
<223> OTHER INFORMATION: oligonucleotide

<400> SEQUENCE: 21
ggatccatga atcccaactt caacagtg                                       28

<210> SEQ ID NO 22
<211> LENGTH: 31
<212> TYPE: DNA
<213> ORGANISM: Artificial
<220> FEATURE:
<223> OTHER INFORMATION: oligonucleotide

<400> SEQUENCE: 22
gaattcttat cggttatata tctggctctc c                                   31

<210> SEQ ID NO 23
<211> LENGTH: 23
<212> TYPE: DNA
<213> ORGANISM: Artificial
<220> FEATURE:
<223> OTHER INFORMATION: oligonucleotide

<400> SEQUENCE: 23
tgctgctcat gcgcatgggg ctg                                            23
```

```
<210> SEQ ID NO 24
<211> LENGTH: 28
<212> TYPE: DNA
<213> ORGANISM: Artificial
<220> FEATURE:
<223> OTHER INFORMATION: oligonucleotide

<400> SEQUENCE: 24
ttagaagcak gcatgwctac actsagcc                                        28

<210> SEQ ID NO 25
<211> LENGTH: 23
<212> TYPE: DNA
<213> ORGANISM: Artificial
<220> FEATURE:
<223> OTHER INFORMATION: oligonucleotide

<400> SEQUENCE: 25
atgcacatgg gaagggtcat gtc                                             23

<210> SEQ ID NO 26
<211> LENGTH: 28
<212> TYPE: DNA
<213> ORGANISM: Artificial
<220> FEATURE:
<223> OTHER INFORMATION: oligonucleotide

<400> SEQUENCE: 26
ttagaagcak gcatgwctac actsagcc                                        28

<210> SEQ ID NO 27
<211> LENGTH: 20
<212> TYPE: DNA
<213> ORGANISM: Artificial
<220> FEATURE:
<223> OTHER INFORMATION: oligonucleotide

<400> SEQUENCE: 27
gcatagcagg agtggagggc                                                 20

<210> SEQ ID NO 28
<211> LENGTH: 21
<212> TYPE: DNA
<213> ORGANISM: Artificial
<220> FEATURE:
<223> OTHER INFORMATION: oligonucleotide

<400> SEQUENCE: 28
gaagcaggca tgactacact c                                               21

<210> SEQ ID NO 29
<211> LENGTH: 20
<212> TYPE: DNA
<213> ORGANISM: Artificial
<220> FEATURE:
<223> OTHER INFORMATION: oligonucleotide

<400> SEQUENCE: 29
tggccaatgt cgcctccgag                                                 20

<210> SEQ ID NO 30
<211> LENGTH: 28
<212> TYPE: DNA
<213> ORGANISM: Artificial
<220> FEATURE:
<223> OTHER INFORMATION: oligonucleotide

<400> SEQUENCE: 30
```
ttagaagcak gcatgwctac actsagcc                                    28

<210> SEQ ID NO 31
<211> LENGTH: 22
<212> TYPE: DNA
<213> ORGANISM: Artificial
<220> FEATURE:
<223> OTHER INFORMATION: oligonucleotide

<400> SEQUENCE: 31
atggctggct atggtgttga tg                                          22

<210> SEQ ID NO 32
<211> LENGTH: 21
<212> TYPE: DNA
<213> ORGANISM: Artificial
<220> FEATURE:
<223> OTHER INFORMATION: oligonucleotide

<400> SEQUENCE: 32
gtgcagtttg caggtaagcc c                                           21

<210> SEQ ID NO 33
<211> LENGTH: 25
<212> TYPE: DNA
<213> ORGANISM: Artificial
<220> FEATURE:
<223> OTHER INFORMATION: oligonucleotide

<400> SEQUENCE: 33
tgtacgcctg acttggctag caacc                                       25

<210> SEQ ID NO 34
<211> LENGTH: 28
<212> TYPE: DNA
<213> ORGANISM: Artificial
<220> FEATURE:
<223> OTHER INFORMATION: oligonucleotide

<400> SEQUENCE: 34
ttagaagcak gcatgwctac actsagcc                                    28

<210> SEQ ID NO 35
<211> LENGTH: 22
<212> TYPE: DNA
<213> ORGANISM: Artificial
<220> FEATURE:
<223> OTHER INFORMATION: oligonucleotide

<400> SEQUENCE: 35
gcaacgtacc gtacctttcc ga                                          22

<210> SEQ ID NO 36
<211> LENGTH: 24
<212> TYPE: DNA
<213> ORGANISM: Artificial
<220> FEATURE:
<223> OTHER INFORMATION: oligonucleotide

<400> SEQUENCE: 36
acgctgcatt caattaccgg gaag                                        24

<210> SEQ ID NO 37
<211> LENGTH: 24
<212> TYPE: DNA
<213> ORGANISM: Artificial

```
<220> FEATURE:
<223> OTHER INFORMATION: oligonucleotide

<400> SEQUENCE: 37
acacctcaaa tagatatgga tata                                          24

<210> SEQ ID NO 38
<211> LENGTH: 29
<212> TYPE: DNA
<213> ORGANISM: Artificial
<220> FEATURE:
<223> OTHER INFORMATION: oligonucleotide

<400> SEQUENCE: 38
gttatctatt ctattctatc atatctatc                                     29

<210> SEQ ID NO 39
<211> LENGTH: 30
<212> TYPE: DNA
<213> ORGANISM: Artificial
<220> FEATURE:
<223> OTHER INFORMATION: oligonucleotide

<400> SEQUENCE: 39
gatatagata tatagaagag atatagatgg                                    30

<210> SEQ ID NO 40
<211> LENGTH: 29
<212> TYPE: DNA
<213> ORGANISM: Artificial
<220> FEATURE:
<223> OTHER INFORMATION: oligonucleotide

<400> SEQUENCE: 40
gttatctatt ctattctatc atatctatc                                     29

<210> SEQ ID NO 41
<211> LENGTH: 29
<212> TYPE: DNA
<213> ORGANISM: Artificial
<220> FEATURE:
<223> OTHER INFORMATION: oligonucleotide

<400> SEQUENCE: 41
agatagatat gatagaatag atagataac                                     29

<210> SEQ ID NO 42
<211> LENGTH: 29
<212> TYPE: DNA
<213> ORGANISM: Artificial
<220> FEATURE:
<223> OTHER INFORMATION: oligonucleotide

<400> SEQUENCE: 42
gttatctatt ctattctatc atatctatc                                     29

<210> SEQ ID NO 43
<211> LENGTH: 28
<212> TYPE: DNA
<213> ORGANISM: Artificial
<220> FEATURE:
<223> OTHER INFORMATION: oligonucleotide

<400> SEQUENCE: 43
attttgtcta aagagactaa atcactgc                                      28
```

<210> SEQ ID NO 44
<211> LENGTH: 29
<212> TYPE: DNA
<213> ORGANISM: Artificial
<220> FEATURE:
<223> OTHER INFORMATION: oligonucleotide

<400> SEQUENCE: 44
gttatctatt ctattctatc atatctatc                              29

<210> SEQ ID NO 45
<211> LENGTH: 24
<212> TYPE: DNA
<213> ORGANISM: Artificial
<220> FEATURE:
<223> OTHER INFORMATION: oligonucleotide

<400> SEQUENCE: 45
acacctcaaa tagatatgga tata                                   24

<210> SEQ ID NO 46
<211> LENGTH: 38
<212> TYPE: DNA
<213> ORGANISM: Artificial
<220> FEATURE:
<223> OTHER INFORMATION: oligonucleotide

<400> SEQUENCE: 46
ccaattcact gggttatcta ttctattcta tcatatct                    38

<210> SEQ ID NO 47
<211> LENGTH: 24
<212> TYPE: DNA
<213> ORGANISM: Artificial
<220> FEATURE:
<223> OTHER INFORMATION: oligonucleotide

<400> SEQUENCE: 47
acacctcaaa tagatatgga tata                                   24

<210> SEQ ID NO 48
<211> LENGTH: 38
<212> TYPE: DNA
<213> ORGANISM: Artificial
<220> FEATURE:
<223> OTHER INFORMATION: oligonucleotide

<400> SEQUENCE: 48
ccaattcact ggccatctat atcttctata tatctata                    38

<210> SEQ ID NO 49
<211> LENGTH: 24
<212> TYPE: DNA
<213> ORGANISM: Artificial
<220> FEATURE:
<223> OTHER INFORMATION: oligonucleotide

<400> SEQUENCE: 49
acacctcaaa tagatatgga tata                                   24

<210> SEQ ID NO 50
<211> LENGTH: 38
<212> TYPE: DNA
<213> ORGANISM: Artificial
<220> FEATURE:
<223> OTHER INFORMATION: oligonucleotide

<400> SEQUENCE: 50

```
ccaattcact ggccccttgt tatatctata tctatacc                               38
```

<210> SEQ ID NO 51
<211> LENGTH: 1041
<212> TYPE: DNA
<213> ORGANISM: Zea mays
<220> FEATURE:
<221> NAME/KEY: misc_feature
<223> OTHER INFORMATION: MRP1

<400> SEQUENCE: 51

```
ctgtaacaac ttgtgtagta cttaacccct cgcacctcat gaatcccaac ttcaacagtg        60
tgtggagcgc tcccgagatc aatatgatga actcactcat cactagtcac atcgccaaca       120
acacctacac aaacaacaac cagcatgttg tggcaagtcg tagtgccatt gtgaaccaca       180
ataactttgg gatgccaacg gaggtcgttc cacccgtgga caacatggac atgatgcaag       240
gctatctaat ggctgatacg gatgccatga ggcttgttca gggacaacaa catatgccaa       300
atgttgttcc taatcaaagg aggcatgcag tgaagttttg gactacagat gagcacagga       360
atttccttcg tggtctagaa gtgtttggcc gtggtaaatg gaagaacatc tccaagtact       420
tcgtccccac aaggacacca gtgcagatct ctagccatgc acagaagtat ttccgcaggc       480
aggagtgcac cacagagaaa caacgcttta gcatcaacga tgttggcctc tacgacacac       540
agccatgggt gcggcagaac aactcctcta gcagctggga ggcgctcacc ttcactgctg       600
gccgtgcgta caataataca aactactgtg cctttaacag cctcccgtat gccagcagcc       660
aggcaagtaa caaccaggta gctacatgga ttacagacca gcaggcaact gcaagttctt       720
ctatagctcc tccagcgacg gaggagagcc agatatataa ccgataatat atataatggt       780
catcagcagc tgggagaggc tttcttcata tataatcaat aggtagatag atatggacaa       840
cgtccattga ctagtttaat ttctatctat atgttttgta tccaatgatg catgtaaaac       900
ctagttggtt gttaaaggtc attagtacca tactatatat gggctagaaa cagtttcatt       960
gaaatttgcc cctgagcaat acaatgaaat tttaccaatg tgttatttat atattaatgt      1020
gtctaaaaaa aaaaaaaaaa a                                                1041
```

<210> SEQ ID NO 52
<211> LENGTH: 242
<212> TYPE: PRT
<213> ORGANISM: Zea mays
<220> FEATURE:
<221> NAME/KEY: MISC_FEATURE
<223> OTHER INFORMATION: MRP1

<400> SEQUENCE: 52

```
Met Asn Pro Asn Phe Asn Ser Val Trp Ser Ala Pro Glu Ile Asn Met
1               5                   10                  15

Met Asn Ser Leu Ile Thr Ser His Ile Ala Asn Asn Thr Tyr Thr Asn
            20                  25                  30

Asn Asn Gln His Val Val Ala Ser Arg Ser Ala Ile Val Asn His Asn
        35                  40                  45

Asn Phe Gly Met Pro Thr Glu Val Val Pro Val Asp Asn Met Asp
    50                  55                  60

Met Met Gln Gly Tyr Leu Met Ala Asp Thr Asp Ala Met Arg Leu Val
65                  70                  75                  80

Gln Gly Gln Gln His Met Pro Asn Val Val Pro Asn Gln Arg Arg His
                85                  90                  95

Ala Val Lys Phe Trp Thr Thr Asp Glu His Arg Asn Phe Leu Arg Gly
```

```
                                100                   105                   110
Leu Glu Val Phe Gly Arg Gly Lys Trp Lys Asn Ile Ser Lys Tyr Phe
            115                   120                   125

Val Pro Thr Arg Thr Pro Val Gln Ile Ser Ser His Ala Gln Lys Tyr
130                   135                   140

Phe Arg Arg Gln Glu Cys Thr Thr Glu Lys Gln Arg Phe Ser Ile Asn
145                   150                   155                   160

Asp Val Gly Leu Tyr Asp Thr Gln Pro Trp Val Arg Gln Asn Asn Ser
                165                   170                   175

Ser Ser Ser Trp Glu Ala Leu Thr Phe Thr Ala Gly Arg Ala Tyr Asn
            180                   185                   190

Asn Thr Asn Tyr Cys Ala Phe Asn Ser Leu Pro Tyr Ala Ser Ser Gln
            195                   200                   205

Ala Ser Asn Asn Gln Val Ala Thr Trp Ile Thr Asp Gln Gln Ala Thr
            210                   215                   220

Ala Ser Ser Ser Ile Ala Pro Pro Ala Thr Glu Glu Ser Gln Ile Tyr
225                   230                   235                   240

Asn Arg

<210> SEQ ID NO 53
<211> LENGTH: 83
<212> TYPE: PRT
<213> ORGANISM: Zea mays
<220> FEATURE:
<221> NAME/KEY: MISC_FEATURE
<223> OTHER INFORMATION: MEG1-3, second ORF

<400> SEQUENCE: 53

Met Gln Trp Leu Ala Phe Val Ala Pro Arg Trp Arg Cys Val Cys Asp
1               5                   10                  15

Gln Glu Leu Ser Ala Gln Thr Gly His Val Thr Asp Asp Val Gly Val
            20                  25                  30

Ser Thr Pro Ala Lys Glu Gly Ile Met Gln Gly Asn Gly Ala Arg Cys
        35                  40                  45

Asp Val Gly Phe Pro Pro Cys Lys Asp Asn Lys Cys Tyr Cys Cys Ile
    50                  55                  60

Gly Gly Arg Thr His Ala Arg Tyr Ser Thr Leu Ala Glu Cys Ser His
65                  70                  75                  80

Ala Cys Phe

<210> SEQ ID NO 54
<211> LENGTH: 16
<212> TYPE: PRT
<213> ORGANISM: Artificial
<220> FEATURE:
<223> OTHER INFORMATION: peptide

<400> SEQUENCE: 54

Pro Cys Lys Asp Asn Lys Cys Tyr Cys Cys Ile Gly Gly Arg Thr His
1               5                   10                  15

<210> SEQ ID NO 55
<211> LENGTH: 23
<212> TYPE: DNA
<213> ORGANISM: Artificial
<220> FEATURE:
<223> OTHER INFORMATION: oligonucleotide

<400> SEQUENCE: 55
gggccaacag ttcctgatta acc                                              23
```

<210> SEQ ID NO 56
<211> LENGTH: 20
<212> TYPE: DNA
<213> ORGANISM: Artificial
<220> FEATURE:
<223> OTHER INFORMATION: oligonucleotide

<400> SEQUENCE: 56
ccccgttgac tgcctcttcg        20

<210> SEQ ID NO 57
<211> LENGTH: 37
<212> TYPE: DNA
<213> ORGANISM: Artificial
<220> FEATURE:
<223> OTHER INFORMATION: MEG promoters conserved sequence

<400> SEQUENCE: 57
atatagatag atatagcaaa ttcaccaaat aatatag        37

<210> SEQ ID NO 58
<211> LENGTH: 1350
<212> TYPE: DNA
<213> ORGANISM: Zea mays
<220> FEATURE:
<221> NAME/KEY: misc_feature
<223> OTHER INFORMATION: MEG1-1 genomic sequence

<400> SEQUENCE: 58

| | | | | | |
|---|---|---|---|---|---|
| ctagttcagt | aataggtgtc | gaggtgttct | cagagttcca | gtacttcgac | gagttaggat | 60 |
| aggctaggac | atcccctagt | cagctgcctg | tggtgggtta | atttacgttg | gcttcgtttc | 120 |
| aattctgtgt | actttgattt | atattatgta | aattactcta | gtcttttata | ttatttctta | 180 |
| ctctttattg | ttattcgaag | cattgtgtta | tgatgagtca | tttatgtaat | tgctatgtac | 240 |
| gtgagttttg | atcctagcac | gtacatggtt | cgcattcggt | ttaccttcta | aaacctgggg | 300 |
| tgacaggtgg | catagcagga | gtggagggca | gcgacggctg | cacagctctg | cgtgcagtgg | 360 |
| cttgcattgt | ttgctcctcg | ttggcgatgc | gtgtgcgacc | atgagctctc | gacacaggta | 420 |
| ggtagtagta | gagccagaat | tgtaaccttg | ggttttccca | cacctcaaat | agatatagat | 480 |
| atagggatat | agatagatat | agcaaattca | ccaaataata | taggggtata | gatatagata | 540 |
| taagaagggg | tatagatata | gatatagata | tatagaagat | atagatagat | agatagatat | 600 |
| gatagaatag | ataacttaca | attttgtcta | aaagaaacta | aatcactgct | aagtttggag | 660 |
| tagcatatct | ttggtgaata | cttgctagtg | aattggtttc | cgctatagta | tatatatata | 720 |
| agtatacact | cttctaggat | tatagtatat | atatatatat | aagtatacac | tcttctagga | 780 |
| tcaatcgtga | ggagttcatt | aaattgtctt | gcgacatgga | gtacagaaag | agggtggatg | 840 |
| cgctagtgtt | tttctcgtta | cttctcctcg | gatactttgc | tgctcatgca | catgggaagg | 900 |
| gtaagtgaaa | actatacaga | catgtgtgtg | catgcttaga | tagatctaga | caatttagaa | 960 |
| gatgttatta | tatgataccg | tgtgtatcat | ggcgaattgc | taatgtatcg | caatcccctg | 1020 |
| tgttaaatta | ctcaaataat | ttcgaatgta | attattctcg | aggcatttgt | tggtaataga | 1080 |
| actcttatcc | tataccttct | actaggtcat | gtcacagatg | atgtcagtgt | ttctactcca | 1140 |
| gctaaagaag | gaattatgca | aggaaacgga | gcacgatgcg | ttgtagggtt | tcctccatgc | 1200 |
| aaagataaca | agtgctactg | ctgcattggg | gggcgaactc | atgctcgcta | ctctcgatgg | 1260 |
| ctgatgtaga | catgcctgct | tctaacaaaa | taagacgttg | tatatatcat | gtatggagga | 1320 |

```
atttataata ttatggaatt agttgtatat                                    1350

<210> SEQ ID NO 59
<211> LENGTH: 127
<212> TYPE: DNA
<213> ORGANISM: Artificial
<220> FEATURE:
<223> OTHER INFORMATION: oligonucleotide
<220> FEATURE:
<221> NAME/KEY: misc_feature
<223> OTHER INFORMATION: nucleotides 1-127 of promoter MEG1-1

<400> SEQUENCE: 59
agccagaatt gtaaccttgg gttttcccac acctcaaata gatatggata tagttatata    60
gatagatata gcaaattcac caaataatat agaggtatag atatagatat aacaaggggt   120
atatata                                                             127

<210> SEQ ID NO 60
<211> LENGTH: 25
<212> TYPE: DNA
<213> ORGANISM: Artificial
<220> FEATURE:
<223> OTHER INFORMATION: oligonucleotide

<400> SEQUENCE: 60
acacctcaaa tagatatgga tatag                                         25

<210> SEQ ID NO 61
<211> LENGTH: 25
<212> TYPE: DNA
<213> ORGANISM: Artificial
<220> FEATURE:
<223> OTHER INFORMATION: oligonucleotide

<400> SEQUENCE: 61
gtcgcaagaa atgttaagga actcc                                         25

<210> SEQ ID NO 62
<211> LENGTH: 500
<212> TYPE: DNA
<213> ORGANISM: Zea mays

<400> SEQUENCE: 62
caggagtgga gggcagcgac ggctgcacag ctctgcgtgc agtggcttgc attgtttgct    60
cctcgttggc gatgcgtgtg cgaccatgag ctctcgacac aggtaggtag tagtagagcc   120
agaattgtaa ccttgggttt tcccacacct caaatagata tagatatagg gatatagata   180
gatatagcaa attcaccaaa taatataggg gtatagatat agatataaga agggtatag    240 atatagatat agatatatag aagatataga tagatagata gatatgatag aatagataac   300
ttacaatttt gtctaaaaga aactaaatca ctgctaagtt tggagtagca tatctttggt   360
gaatacttgc tagtgaattg gtttccgcta tagtatatat atataagtat acactcttct   420
aggattatag tatatatata tatataagta tacactcttc taggatcaat cgtgaggagt   480
tcattaaatt gtcttgcgac                                               500

<210> SEQ ID NO 63
<211> LENGTH: 32
<212> TYPE: DNA
<213> ORGANISM: Artificial
<220> FEATURE:
<223> OTHER INFORMATION: oligonucleotide

<400> SEQUENCE: 63
```

```
atcgatgaat cgctcaagg gtttcttcca tg                              32
```

<210> SEQ ID NO 64
<211> LENGTH: 30
<212> TYPE: DNA
<213> ORGANISM: Artificial
<220> FEATURE:
<223> OTHER INFORMATION: oligonucleotide

<400> SEQUENCE: 64

```
ggatcctcga gcctctagta tcggtctgac                                30
```

<210> SEQ ID NO 65
<211> LENGTH: 93
<212> TYPE: PRT
<213> ORGANISM: Zea mays

<400> SEQUENCE: 65

Met Ala Lys Phe Phe Asn Tyr Thr Ile Ile Gln Gly Leu Leu Met Leu
1               5                   10                  15
Ser Met Val Leu Leu Ala Ser Cys Ala Ile His Ala His Ile Ile Ser
            20                  25                  30
Gly Glu Thr Glu Glu Val Ser Asn Thr Gly Ser Pro Thr Val Met Val
        35                  40                  45
Thr Met Gly Ala Asn Arg Lys Ile Ile Glu Asp Asn Lys Asn Leu Leu
    50                  55                  60
Cys Tyr Leu Arg Ala Leu Glu Tyr Cys Cys Ala Arg Thr Arg Gln Cys
65                  70                  75                  80
Tyr Asp Asp Ile Lys Lys Cys Leu Glu His Cys Arg Gly
                85                  90

<210> SEQ ID NO 66
<211> LENGTH: 76
<212> TYPE: PRT
<213> ORGANISM: Zea mays

<400> SEQUENCE: 66

Met Leu Ser Met Val Leu Leu Ala Ser Cys Val Ile His Ala His Ile
1               5                   10                  15
Ile Ser Gly Glu Ile Glu Asp Val Ser Asn Thr Arg Ser Pro Thr Met
            20                  25                  30
Met Gly Ala Asn Arg Lys Ile Ile Gly Asp Asn Lys Asn Leu Leu Cys
        35                  40                  45
Tyr Leu Lys Ala Leu Glu Tyr Cys Cys Glu Arg Thr Lys Gln Cys Tyr
    50                  55                  60
Asp Asp Ile Lys Lys Cys Leu Glu His Cys His Ser
65                  70                  75

<210> SEQ ID NO 67
<211> LENGTH: 95
<212> TYPE: PRT
<213> ORGANISM: Zea mays

<400> SEQUENCE: 67

Met Ala Lys Cys Ser Ser Phe Gln Gly Leu Phe Trp Leu Leu Ser Met
1               5                   10                  15
Ile Leu Leu Ala Ser Phe Val Ala His Ala Arg Thr Thr Ser Gly Gln
            20                  25                  30
Thr Lys Glu Asp Ser Asn Ala Arg Asn Met Thr Met Thr Lys Thr Arg
        35                  40                  45

```
Ala Ser Gly Asn Ile Leu Val Ser Arg Asn Asp Asp Gly Pro Cys Tyr
     50                  55                  60

Leu Asp Ser Gly Leu Asn Glu Tyr Val Cys Arg Lys Thr Asn Lys Cys
 65                  70                  75                  80

Tyr Lys Ser Leu Val Leu Cys Val Ala Ser Cys Gln Pro Ser Ser
             85                  90                  95

<210> SEQ ID NO 68
<211> LENGTH: 93
<212> TYPE: PRT
<213> ORGANISM: Zea mays

<400> SEQUENCE: 68

Met Ala Lys Phe Phe Asn Tyr Thr Ile Val Gln Gly Leu Leu Met Leu
 1               5                  10                  15

Ser Met Val Leu Leu Ala Ser Cys Val Ile His Ala His Ile Ile Ser
             20                  25                  30

Gly Glu Thr Glu Glu Val Ser Asn Ile Gly Ser Pro Thr Val Met Val
         35                  40                  45

Thr Met Gly Ala Asn Arg Lys Ile Ile Gly Asp Asn Lys Asn Leu Leu
 50                  55                  60

Cys Tyr Leu Lys Ala Leu Glu Tyr Cys Cys Glu Arg Thr Lys Gln Cys
 65                  70                  75                  80

Tyr Asp Asp Ile Lys Lys Cys Leu Glu His Cys His Gly
             85                  90

<210> SEQ ID NO 69
<211> LENGTH: 91
<212> TYPE: PRT
<213> ORGANISM: Zea mays

<400> SEQUENCE: 69

Met Ala Arg Cys Leu Lys Ser Cys Ser Val His Gly Leu Trp Leu Leu
 1               5                  10                  15

Ser Met Ile Leu Leu Ala Ser Cys Val Val His Ala His Ile Ile Asn
             20                  25                  30

Gly Arg Gln Ser Asn Thr Gly Ser Leu Thr Met Thr Thr Thr Gly Glu
         35                  40                  45

Ala Ser Met Ile Ile Gly Asp Glu Lys Asp Ala Ile Cys Tyr Ile Lys
 50                  55                  60

Ala Ala Leu Tyr Cys Cys Lys Arg Thr Ile Gln Cys Tyr Gln Asp Ile
 65                  70                  75                  80

Ala Gln Cys Leu Arg Asn Cys Arg Lys Asn Val
             85                  90

<210> SEQ ID NO 70
<211> LENGTH: 84
<212> TYPE: PRT
<213> ORGANISM: Artificial Sequence
<220> FEATURE:
<223> OTHER INFORMATION: Synthetic consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
```

```
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (61)..(63)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid

<400> SEQUENCE: 70

Val Xaa Gly Leu Leu Met Leu Ser Met Val Leu Leu Ala Ser Cys Val
1               5                   10                  15

Ile His Ala His Ile Ile Ser Gly Xaa Thr Xaa Asp Xaa Ser Asn Xaa
            20                  25                  30

Xaa Ser Pro Thr Xaa Xaa Xaa Thr Met Gly Ala Asn Arg Xaa Ile Ile
        35                  40                  45

Gly Asp Asn Lys Xaa Xaa Leu Cys Tyr Leu Lys Ala Xaa Xaa Xaa Glu
    50                  55                  60

Tyr Cys Cys Xaa Arg Thr Xaa Gln Cys Tyr Xaa Asp Ile Xaa Xaa Cys
65                  70                  75                  80

Leu Xaa Xaa Cys
```